US012673996B2

(12) United States Patent
Zhou et al.

(10) Patent No.: US 12,673,996 B2
(45) Date of Patent: Jul. 7, 2026

(54) PROTEIN CONTAINING HETERODIMER ANTIBODY FC, AND PREPARATION METHOD THEREFOR

(71) Applicant: INNOVENT BIOLOGICS (SUZHOU) CO., LTD., Suzhou (CN)

(72) Inventors: Shuaixiang Zhou, Suzhou (CN); Fenggen Fu, Suzhou (CN)

(73) Assignee: INNOVENT BIOLOGICS (SUZHOU) CO., LTD., Suzhou (CN)

( * ) Notice: Subject to any disclaimer, the term of this patent is extended or adjusted under 35 U.S.C. 154(b) by 515 days.

(21) Appl. No.: 18/258,047

(22) PCT Filed: Dec. 30, 2021

(86) PCT No.: PCT/CN2021/143141
§ 371 (c)(1),
(2) Date: Jun. 16, 2023

(87) PCT Pub. No.: WO2022/143912
PCT Pub. Date: Jul. 7, 2022

(65) Prior Publication Data
US 2024/0034795 A1 Feb. 1, 2024

(30) Foreign Application Priority Data
Dec. 31, 2020 (CN) .......................... 202011644192.1

(51) Int. Cl.
| | |
|---|---|
| C07K 16/00 | (2006.01) |
| C07K 14/55 | (2006.01) |
| C07K 16/28 | (2006.01) |
| C07K 16/30 | (2006.01) |
| C07K 16/32 | (2006.01) |

(52) U.S. Cl.
CPC .......... *C07K 16/2818* (2013.01); *C07K 14/55* (2013.01); *C07K 16/2887* (2013.01); *C07K 16/303* (2013.01); *C07K 16/32* (2013.01); C07K 2317/31 (2013.01); C07K 2317/526 (2013.01); C07K 2317/92 (2013.01); C07K 2317/94 (2013.01); C07K 2319/31 (2013.01); C07K 2319/33 (2013.01)

(58) Field of Classification Search
None
See application file for complete search history.

(56) References Cited

U.S. PATENT DOCUMENTS

| | | | |
|---|---|---|---|
| 7,919,086 B2 | 4/2011 | Nakano et al. | |
| 2012/0149876 A1 | 6/2012 | Von Kreudenstein et al. | |
| 2013/0336973 A1* | 12/2013 | Spreter Von Kreudenstein | .......... C07K 16/2863 435/375 |
| 2018/0237541 A1 | 8/2018 | Kim et al. | |
| 2019/0367628 A1 | 12/2019 | Abujoub et al. | |

FOREIGN PATENT DOCUMENTS

| | | |
|---|---|---|
| CA | 3140142 A1 | 11/2020 |
| CN | 103429620 A | 12/2013 |
| CN | 104080811 A | 10/2014 |
| CN | 109422811 A | 3/2019 |
| CN | 109970860 A | 7/2019 |
| CN | 110662555 A | 1/2020 |
| CN | 111315778 A | 6/2020 |
| CN | 115698052 A | 2/2023 |
| WO | 9627011 A1 | 9/1996 |
| WO | 1998050431 A2 | 11/1998 |
| WO | 2013063702 A1 | 5/2013 |
| WO | 2013097430 A1 | 7/2013 |
| WO | 2017024465 A1 | 2/2017 |
| WO | 2019231920 A1 | 12/2019 |
| WO | 2020014505 A1 | 1/2020 |
| WO | 20200236797 A1 | 11/2020 |

OTHER PUBLICATIONS

Choi et al., Engineering of Immunoglobulin Fc Heterodimers Using Yeast Surface-Displayed Combinatorial Fc Library Screening, PLoS ONE, 10 (12): e0145349, 2015, 20 pages.
Fan et al. "Bispecific antibodies and their applications", Journal Hematology & Oncology, vol. 8, No. 130, 2015, 14 pages.
Gerngross. "Advances in the production of human therapeutic proteins in yeasts and filamentous fungi", Nature Biotechnology, 2004, vol. 22, No. 11, p. 1409-1414.
Gunasekaran et al., "Enhancing antibody Fc heterodimer formation through electrostatic steering effects: applications to bispecific molecules and monovalent IgG", Journal of Biological Chemistry, vol. 285, No. 25, 2010, p. 19637-19646.
Ionescu et al., "Contribution of variable domains to the stability of humanized IgG1 monoclonal antibodies", Journal of Pharmaceutical Sciences, vol. 97, No. 4, 2008, p. 1414-1426.
International Search Report and Written Opinion of PCT/CN2021/143141, mailed Mar. 29, 2022. [21 pages].
Muda et al. "Therapeutic assessment of SEED: a new engineered antibody platform designed to generate mono- and bispecific antibodies", Protein Engineering, Design & Selection, vol. 24, No. 5, 2011, p. 447-454.

* cited by examiner

*Primary Examiner* — Chun W Dahle
(74) *Attorney, Agent, or Firm* — LEASON ELLIS LLP

(57) ABSTRACT

The present invention relates to novel proteins containing heterodimeric antibody Fc such as bispecific antibodies, and novel methods for preparing such proteins.

14 Claims, 5 Drawing Sheets
Specification includes a Sequence Listing.

PROTEIN CONTAINING HETERODIMER ANTIBODY FC, AND PREPARATION METHOD THEREFOR

BACKGROUND

The present invention relates to novel heterodimeric Fc scaffolds, novel Fc heterodimeric proteins comprising the heterodimeric Fc scaffolds such as bispecific antibodies or Fc region fusion proteins, and novel methods for preparing such proteins.

Antibody molecules dominate in the biopharmaceutics industry. Bispecific antibodies (bsAbs), as individual molecules, bind to two different antigens or two different epitopes on one antigen simultaneously. They are distinct from natural immunoglobulin G (IgG) monospecific antibodies (mAbs). With additional targeting capabilities, bsAbs generally provide improved clinical benefits for the treatment of complex diseases (such as cancer and immune disorders) involving multiple cell surface receptors or ligands. Efforts have been made to engineer mAbs into bsAbs, and more than 60 different bsAb forms have been produced. Many bsAbs can be engineered by linking antibody fragments, such as single chain variable fragments (scFv), antigen-binding fragments (Fab) and heavy chain and light chain variable domains (VH and VL). However, such new forms, which differ from conventional IgG structures, generally possess undesirable physicochemical properties, such as poor solubility and aggregation, thus having difficulty in large-scale production, poor thermostability and pharmacokinetics, and potential immunogenicity. The great production challenges of bispecific antibodies in terms of quantity, quality and stability have hindered their further clinical application and acceptance.

Heterodimeric Fc technology has been developed to aid in the production of bispecific antibodies. For example, Carter et al., have successfully produced bispecific antibodies by engineering part of the amino acids in the antibody heavy chain using the "Kih" (knobs-into-holes) model (Ridgway, Presta, et al., 1996; Carter, 2001). They created a "knob" (e.g., T366Y) by mutating an amino acid with a small side chain to an amino acid with a large side chain in the CH3 region of the first heavy chain of the Fc and created a "hole" (Y407T, etc.) by mutating some amino acids in CH3 region of the second heavy chain to amino acids with a small side chain, i.e., realized the formation of heterodimer through spatial conformational complementarity. The proportion of the heterodimer was further improved by methods such as random mutation-phage display and the like, and disulfide bonds were introduced in the CH3 region to improve the stability of the heterodimer. However, the capacity of hindering the formation of homodimers was still insufficient, and the proportion of the heterodimer was about 70-80%.

Alternatively, strand-exchange engineered domain (SEED) heterogeneity represents another spatial mutation-based design strategy, which employs alternative amino acid sequences in IgG and IgA CH3 domains (AG SEED CH3 and GA SEED CH3) to form complementary structures. Due to the complementary sequences in IgG and IgA CH3 derivatives, the two complementary heavy chains can be assembled to produce a heterodimer, thereby eliminating the possibility of producing homodimers due to the lack of complementarity (Muda, M, et al., Therapeutic assessment of SEED: A new engineered antibody platform designed to generate mono- and bispecific antibodies. *Protein Eng. Des. Sel.* (*PEDS*), 2011, 24, 447-454).

In addition to the spatial mutations proposed earlier, electrostatic interaction has also been widely used to promote heterodimer formation in the heavy chain. The process mutates individual amino acids in the CH3 domain of one heavy chain into Lys carrying a positive charge, and individual amino acids in the CH3 of the other heavy chain into Asp or Glu carrying a negative charge. The charged amino acids then readily form heterodimers by electrostatic attraction. Gunasekaran et al. first introduced charged amino acids to form Fc-heterodimeric bispecific antibodies (Gunasekaran, K. et al., Enhancing antibody Fc heterodimer formation through electrostatic steering effects: applications to bispecific molecules and monovalent IgG. *J. Biol. Chem.*, 2010, 285, 19637-19646.).

Known site-specific mutations can significantly improve antibody yield and quality, but the capacity to hinder homodimer formation remains insufficient. Also, both spatial mutation and introduction of charged pairs will reduce the thermal stability of bispecific antibodies. Thus, the need for novel heterodimeric Fc scaffolds that can more efficiently produce Fc heterodimers (e.g., bispecific antibodies) comprising the same without reducing the physicochemical properties (e.g., thermostability) of the Fc heterodimers (e.g., bispecific antibodies) remains in the art.

SUMMARY

The present invention, by designing combinations of mutations in the CH3 region based on the crystal structure of CH3 in the Fc region and charge and steric conformational effects, can increase Fc-containing heterodimer formation of the heavy chain of an Fc heterodimeric protein (e.g., a bispecific antibody or an Fc region fusion protein) and optionally does not compromise physicochemical properties of the bispecific antibody, e.g., thermostability.

One aspect of the present invention relates to a novel Fc heterodimer, e.g., a bispecific antibody, comprising: a first antigen-binding region comprising a first Fc region comprising a first CH3 region, and a second antigen-binding region comprising a second Fc region comprising a second CH3 region, wherein the first CH3 region and the second CH3 region are different in sequence, such that the heterodimeric interaction between the first CH3 region and the second CH3 region is stronger than the homodimeric interactions of the first CH3 region and the second CH3 region.

In some embodiments, the first CH3 region comprises an amino acid substitution selected from: T350V/A, E357N/Q, S364R/K, D399K/R, K409E/D and T411R/K.

In some embodiments, the second CH3 region comprises one or more amino acid substitutions selected from: Q347D/E, Y349T/S/A/V, T350V/A, K370T/S/A/V, D399K/R and K409D/E.

In some embodiments, the Fc heterodimer is an Fc bispecific antibody or an Fc region fusion protein.

In some embodiments, the present invention provides a method for preparing an Fc heterodimer.

DETAILED DESCRIPTION

Figure 1:
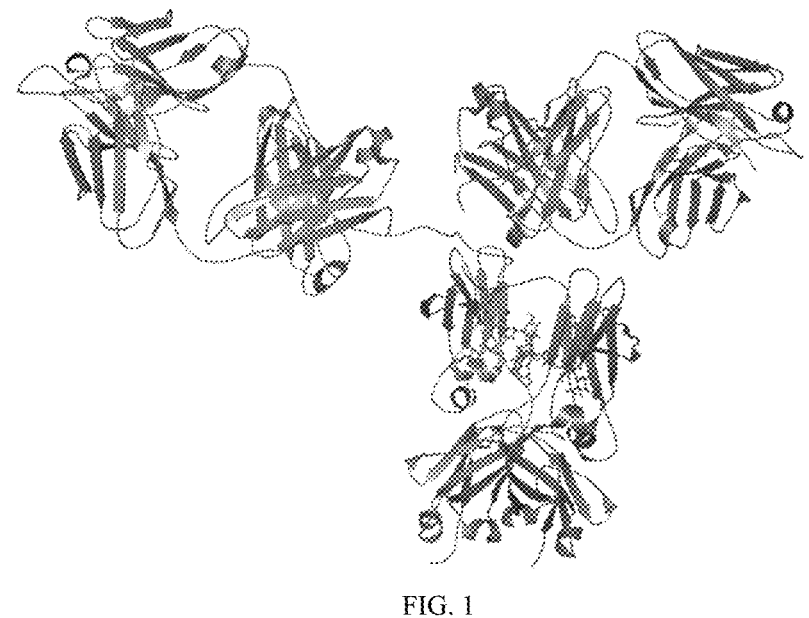
FIG. 1 shows the crystal structure of an antibody (PDB: 1hzh)

Unless otherwise indicated, conventional methods of chemistry, biochemistry, organic chemistry, molecular biology, microbiology, recombinant DNA techniques, genetics, immunology and cell biology that are known in the art will be employed for the implementation of the present invention. Descriptions of such methods can be found, for example, in Sambrook et al., *Molecular Cloning: A Laboratory Manual* (3rd edition, 2001); Sambrook et al., *Molecular Cloning: A Laboratory Manual* (2nd edition, 1989); Maniatis et al., *Molecular Cloning: A Laboratory Manual* (1982); Ausubel et. al., *Current Protocols in Molecular Biology* (John Wiley and Sons, updated in July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I&II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); Harlow and Lane, *Antibodies* (Cold Spring Harbor Laboratory Press, Cold Spring Harbor, N.Y., 1998) *Current Protocols in Immunology* (Q. E. Coligan, A. M. Kruisbeek, D. H. Margulies, E. M. Shevach and W Strober, eds., 1991); *Annual Review of Immunology*; and journals and monographs such as *Advances in Immunology*.

Definitions

Unless defined otherwise, all technical and scientific terms used herein have the same meaning as commonly understood by those of ordinary skills in the art. For the purposes of the present invention, the following terms are defined below.

The term "about" used in combination with a numerical value is intended to encompass the numerical values in a range from a lower limit 5% lower than the specified numerical value to an upper limit 5% higher than the specified numerical value.

The term "and/or", when used to connect two or more options, should be interpreted as any one of the options or any two or more of the options.

As used herein, the term "comprise" or "include" refers to the inclusion of the described elements, integers or procedures, but not to the exclusion of any other elements, integers or procedures. As used herein, the term "comprise" or "include", unless indicated otherwise, also encompasses the situation where the entirety consists of the described elements, integers or procedures. For example, when referring to a polypeptide "comprising" a particular sequence, it is also intended to encompass polypeptides consisting of that particular sequence.

The term "Fc region" is used herein to define the C-terminal region of an immunoglobulin heavy chain, which does not include the heavy chain constant region CH1. An immunoglobulin Fc region generally comprises two constant domains, a CH2 region and a CH3 region, and optionally comprises a CH4 region. Thus, in the present invention, the Fc region may be the last two immunoglobulin constant regions of IgA, IgD and IgG, or the last three immunoglobulin constant regions of IgE and IgM, and optionally the hinge region in the N-terminal direction of these constant regions.

In one embodiment of the present invention, the Fc region comprises a CH2 region and a CH3 region. In a preferred embodiment, the Fc region further comprises amino acid residues of the hinge region. In one embodiment, the Fc region is a human IgG heavy chain Fc region, extending from Glu216 to the carboxy terminus of the heavy chain, wherein a C-terminus lysine (Lys447) in the Fc region may or may not be present. In another embodiment, the Fc region preferably comprises the entire IgG hinge region (EU numbering positions 216-230) and the dimer is formed by disulfide bonds of the hinge region. In one embodiment, the two chains forming the Fc dimer each comprise part or all of the hinge region and the CH2 and CH3 domains.

As used herein, the term Fc region includes Fc regions of native sequences and variant Fc regions. In one embodiment, the Fc region may be an Fc region from any IgG, preferably a mammalian or human IgG Fc region, such as an IgG1, IgG2, IgG3 or IgG4 Fc region. In one embodiment, the amino acid sequence of the Fc region of human IgG1 starts in the hinge region and ends at the carboxy terminus of the CH3 region. The native or wild-type human IgG1 Fc region is intended herein to encompass such native allelic forms.

In this context, the Fc region may be such a region in isolation, or such a region in an antibody, antibody fragment or Fc fusion protein.

Herein, unless otherwise indicated, the numbering of amino acid residues in various regions of an antibody, e.g., the Fc region or constant region, is based on the EU numbering system, as described in Kabat, E. A., et al., *Sequences of Proteins of Immunological Interest*, 5th edition, Public Health Service, National Institutes of Health, Bethesda, MD (1991), NIH Publication 91-3242, of which the sections describing this numbering system are incorporated herein by reference. EU numbering of Fc regions or constant regions can also be readily acquired by searching the EU numbering website: http://www.imgt.org/IMGTScientificChart/Numbering/Hu_IGHGnberhtml. Herein, specific amino acid residues of an antibody IgG constant region are described according to the numbering system. For example, "S364" refers to a serine at EU position 364. An amino acid mutation at a specific position in the constant region is indicated by "original amino acid, amino acid position, mutated amino acid". For example, "S364R" refers to a substitution of serine (S) with arginine (R) at EU position 364. When describing combinations of mutations, the combined mutations are joined by a plus (+) sign. "S364R+D399K" indicates that the Fc region comprises the mutations S364R and D399K. When there is a possibility of more than one mutation at a particular position, it is indicated herein by the sign "/". For example, the mutation "K370T/S" indicates that the residue K at position 370 may be substituted with T or S residue.

"Fc region protein" or "Fc region polypeptide" are used interchangeably herein to refer to a protein or polypeptide comprising an Fc region.

As used herein, "variant Fc region" and "variant Fc" are used interchangeably to refer to an Fc region in which one or more amino acid modifications (i.e., amino acid substitutions, deletions, and/or insertions) are introduced at any position relative to the Fc region prior to modification (i.e., the parent Fc region). In some embodiments, the parent Fc region is a native immunoglobulin Fc region, i.e., a wild-type Fc region. In another embodiment, the parent Fc region is an Fc region in which mutations have been introduced on the basis of the wild-type Fc region. In one embodiment, the parent Fc region comprises an amino acid sequence set forth in SEQ ID NO: 48. In yet another embodiment, the parent Fc region comprises a sequence having at least 85%, 90%, 91%, 92%, 93%, 94%, 95%, 96%, 97%, 98%, 99% or higher percent sequence identity to SEQ ID NO: 48. In some embodiments, the parent Fc region comprises an amino acid sequence in which amino acid mutations changing a property of the Fc region are introduced in a wild-type Fc region such as SEQ ID NO: 48, wherein the property of the Fc may be selected from, but is not limited to, binding affinity to a specific Fc receptor and glycosylation pattern of the Fc, but the parent Fc does not comprise amino acid mutations that alter the properties of Fc heterodimerization. The amino acid mutations may be those known in the art or obtained by the screening methods of the present invention. In some embodiments, the parent Fc region further comprises a hinge region. For example, the hinge region comprises an amino acid sequence set forth in SEQ ID NO: 23.

As used herein, "variant CH3 region" and "variant CH3" are used interchangeably to refer to a CH3 region in which one or more amino acid modifications (i.e., amino acid substitutions, deletions, and/or insertions) are introduced at any position relative to the CH3 region prior to modification (i.e., the parent CH3 region). In some embodiments, the parent CH3 region is derived from a native immunoglobulin Fc region, i.e., the CH3 region of a wild-type Fc region. In another embodiment, the parent CH3 region is a CH3 region in which mutations have been introduced on the basis of the wild-type CH3 region. In one embodiment, the parent CH3 region comprises an amino acid sequence set forth in SEQ ID NO: 49. In yet another embodiment, the parent CH3 region comprises a sequence having at least 85%, 90%, 91%, 92%, 93%, 94%, 95%, 96%, 97%, 98%, 99% or higher percent sequence identity to SEQ ID NO: 49. In some embodiments, the parent CH3 region comprises an amino acid sequence in which amino acid mutations changing a property of the Fc region comprising the CH3 region are introduced in a wild-type CH3 region such as SEQ ID NO: 49, wherein the property of the Fc may be selected from, but is not limited to, binding affinity to a specific Fc receptor and glycosylation pattern of the Fc, but the parent CH3 region does not comprise amino acid mutations that alter the properties of Fc heterodimerization. The amino acid mutations may be those known in the art or obtained by the screening methods of the present invention.

Thus, in some embodiments, the parent Fc region comprises a CH2 region and a CH3 region set forth in SEQ ID NO: 49, and optionally a hinge region.

As used herein, "Fc receptor" refers to any molecule that can bind to the Fc region of an antibody and form an Fc/Fc receptor complex, such as a protein or a polypeptide from an organism. Fc receptors include, but are not limited to, FcγRI, FcγRII, FcγRIII, FcRn, C1q, C3, mannan-binding lectin, mannose receptor, protein A, protein G and viral FcγR. Fc receptors also include Fc receptor homologs (FcRH). FcRH is an Fc receptor homologous to FcγR. Preferably, the Fc receptor is FcRn or FcγR. The binding site of the antibody to FcRn is located at the joint of CH2 and CH3.

Herein, "Fc heterodimer" refers to a protein comprising a polypeptide fused to an Fc region based on the heterodimeric Fc scaffold. For example, the Fc heterodimer can be a protein comprising two target-binding regions, one target-binding region comprising a first Fc region and a target-binding domain fused to the first Fc region (e.g., a heavy and/or light chain variable region of an antibody that can bind to a target molecule, or a soluble moiety of a ligand or receptor that can bind to a target molecule), and the other target-binding region comprising a second Fc region and a target-binding domain fused to the second Fc region (e.g., a heavy and/or light chain variable region of an antibody that can bind to a target molecule, or a soluble moiety of a ligand or receptor that can bind to a target molecule). In some embodiments, the Fc heterodimer is a bispecific antibody. In other embodiments, the Fc heterodimer is an Fc fusion protein.

As used herein, "heterodimeric Fc scaffold" refers to a scaffold comprising two different Fc regions or formed by dimerization of two different Fc regions, which may be linked to a domain that binds a target or an antigen at the N terminus or C terminus (e.g., a heavy and/or light chain variable region of an antibody or an antigen binding fragment of an antibody that can bind to a target molecule, or a soluble moiety of a ligand or receptor that can bind to a target molecule) to construct an Fc heterodimer, e.g., a bispecific antibody or fusion protein. Thus, the "heterodimeric Fc scaffold" described herein includes not only isolated Fc heterodimers, but also heterodimeric Fc regions in Fc heterodimers, e.g., bispecific antibodies or Fc region fusion proteins.

The term "bispecific antibody" refers to an antibody comprising a first binding region and a second binding region, wherein the first binding region binds to one antigen or epitope and the second binding region binds to another antigen or another epitope. Thus, the bispecific antibody according to the present invention comprises specificity for two different antigens, or for two different epitopes of one antigen. The bispecific antibody formats include IgG-like antibodies (Fan et al., (2015) *Journal of Hematology & Oncology.* 8:130). The IgG-like antibodies described herein comprise two Fc regions. The most common form of IgG-like antibodies comprises two Fab regions and two Fc regions, the heavy and light chains of each Fab may be from a separate monoclonal antibody.

The bispecific antibodies of the present invention can be prepared using bispecific antibody formats or techniques known in the art. Specific exemplary bispecific formats that can be used in the context of the present invention include, but are not limited to: one Fab linked to an Fc region+one protein linked to an Fc region (e.g., FIG. 2, format 1), one Fab linked to an Fc region+one scFv linked to an Fc region (e.g., FIG. 2, format 2), one Fab linked to an Fc region+one VHH linked to an Fc region (e.g., FIG. 2, format 3) and one Fab linked to an Fc region+another Fab linked to an Fc region (e.g., FIG. 2, format 4).

The term "linker" as used herein refers to any molecule that enables direct connection of different portions of a bispecific antibody. Examples of linkers to establish covalent linkages between different antibody moieties include peptide linkers and non-proteinaceous polymers including, but not limited to, polyethylene glycol (PEG), polypropylene glycol, polyalkylene oxide and copolymers of polyethylene glycol and polypropylene glycol. The term "peptide linker" according to the present invention refers to an amino acid sequence that links the amino acid sequence of a first portion of an antibody to a second portion of the antibody. For example, the peptide linker may link a first (variable and/or binding) domain of to a second (variable and/or binding) domain of the antibody. For example, the peptide linker may also link one portion of the antibody to another portion of the antibody, for example, an antigen-binding domain to an Fc domain or a fragment thereof. Preferably, the peptide linker has a length sufficient to link two entities in a manner that maintains their conformation relative to each other without interference with the desired activities. The peptide linker may or may not comprise predominantly the following amino acid residues: Gly, Ser, Ala or Thr. Useful linkers include glycine-serine polymers including, for example, (GS)n, (GSGGS)n, (GGGGS)n, (GGGS)n and (GGGGS)nG, where n is an integer of at least 1 (preferably 2, 3, 4, 5, 6, 7, 8, 9 or 10). Useful linkers also include glycine-alanine polymers, alanine-serine polymers, and other flexible linkers.

The term "valent" according to the present invention refers to the specified number of binding sites present in an antibody molecule. Thus, the terms divalent, trivalent and tetravalent indicate the presence of two, three and four binding sites, respectively, in an antibody construct. The bispecific antibodies according to the present invention are at least bivalent and may be multivalent, e.g. bivalent, trivalent, tetravalent or hexavalent.

The term "target-binding region" as used herein refers to any portion of an Fc heterodimer that binds to a particular target (e.g., an antigen). The target-binding region may be, for example, an antibody or immunoglobulin per se or an antibody fragment. Such binding regions may or may not comprise a tertiary structure independent of the other portions of the dimer, and may or may not bind to their targets as separate entities. The "target-binding region" according to the present invention comprises the Fc region. In an Fc heterodimer comprising first and second target-binding regions, the first target-binding region is indicated as "Domain A/domain A" and the second target-binding region is indicated as "Domain B/domain B" herein. In the first target-binding region, the Fc region is referred to as Fc-A; in the second target-binding region, the Fc region is referred to as Fc-B. The first target-binding region and the second target-binding region may have the same or different structures. When the first target-binding region and the second target-binding region have the same structure, e.g., both have an Fab fragment linked to an Fc region, it is said that "the first target-binding region and the second target-binding region are mirror images of each other". When the first target-binding region and the second target-binding region have different structures, for example, the first target-binding region comprises an Fab fragment linked to an Fc region, the second target-binding region comprises a VHH, an scFv or other antigen-binding fragments linked to an Fc region, or comprises another protein (e.g., a ligand) linked to an Fc region, it is said that "the first target-binding region and the second target-binding region are not mirror images of each other".

In certain exemplary embodiments of the present invention, the Fc heterodimer is a bispecific antibody and the target-binding region thereof is an antigen-binding region. Each antigen-binding region of the bispecific antibody comprises a heavy chain variable region VH, a light chain variable region VL and an Fc region. In a bispecific antibody that includes a first antigen-binding region and a second antigen-binding region, domains of the first antigen-binding region such as VH, VL, CDR, Fc region, CH3 and the like may be denoted with suffix "A", and domains of the second antigen-binding region such as VH, VL, CDR, Fc region, CH3 and the like may be denoted with suffix "B". For example, in the first antigen-binding region, the heavy chain is referred to as heavy chain A, the light chain is referred to as light chain A, the heavy chain variable region (VH) is referred to as VH-A, the heavy chain variable region CDRs are referred to herein as VH-A-CDR1/2/3, the Fc region is referred to as Fc-A, CH1, CH2 and CH3 are referred to herein as CH1-A, CH2-A and CH3-A, respectively, the hinge region is referred to as Hinge-A, the light chain variable region (VL) is referred to as VL-A, the light chain variable region CDRs are referred to as VL-A-CDR1/2/3, and the light chain constant region (CL) is referred to as CL-A.

The term "antibody fragment" includes a portion of an intact antibody. In a preferred embodiment, the antibody fragment is an antigen-binding fragment. The "Antigen-binding fragment" refers to a molecule different from an intact antibody, which comprises a portion of the intact antibody and binds to an antigen to which the intact antibody binds. Examples of the antibody fragments include, but are not limited to, Fv, Fab, Fab', Fab'-SH, F(ab')$_2$, a domain antibody (dAb), a linear antibody, a single-chain antibody (e.g., scFv), a single-domain antibody (e.g., VHH), a bi-valent antibody or a fragment thereof, and a camelid anti-body.

The term "antigen" refers to a molecule that induces an immune response. Such an immune response may involve antibody production or activation of specific immune cells, or both. Those skilled in the art will appreciate that any macromolecules, including essentially all proteins or peptides, can be used as antigens. In addition, an antigen may be derived from recombinant or genomic DNA. As used herein, the term "epitope" refers to a portion, which specifically interacts with an antibody molecule, of an antigen. In some embodiments, the antigen is a tumor-associated antigen (i.e., an antigen associated with the development and progression of a tumor). In some embodiments, the antigen is selected from PD1 (or PDL1 or PDL2), CD20, HER2, CD47, GPC3 and the like.

As used herein, the term "sequence identity" refers to the degree to which sequences are identical on a nucleotide-by-nucleotide or amino acid-by-amino acid basis in a comparison window. The "percent sequence identity" can be calculated by the following steps: comparing two optimally aligned sequences in a comparison window; determining the number of positions in which nucleic acid bases (e.g., A, T, C, G and I) or amino acid residues (e.g., Ala, Pro, Ser, Thr, Gly, Val, Leu, Ile, Phe, Tyr, Trp, Lys, Arg, His, Asp, Glu, Asn, Gln, Cys and Met) are the same in the two sequences to give the number of matched positions; dividing the number of matched positions by the total number of positions in the comparison window (i.e., the window size); and multiplying the result by 100 to give a percent sequence identity. Optimal alignment for determining the percent sequence identity can be achieved in a variety of ways known in the art, for example, using publicly available computer software such as BLAST, BLAST-2, ALIGN, or Megalign (DNASTAR) software. Those skilled in the art can determine suitable parameters for the alignment of sequences, including any algorithms necessary to achieve optimal alignment in a full-length sequence range or target sequence region being compared.

"Complementarity determining region" or "CDR region" or "CDR" is a region in an antibody variable domain that is highly variable in sequence and forms a structurally defined loop ("hypervariable loop") and/or comprises antigen-contacting residues ("antigen contact site"). CDRs are primarily responsible for binding to antigen epitopes. The CDRs of the heavy and light chains are generally referred to as CDR1, CDR2 and CDR3, and are numbered sequentially from the N terminus. The CDRs located in the heavy chain variable domain of the antibody are referred to as HCDR1, HCDR2 and HCDR3, whereas the CDRs located in the light chain variable domain of the antibody are referred to as LCDR1, LCDR2 and LCDR3. In a given amino acid sequence of a light chain variable region or a heavy chain variable region, the exact amino acid sequence boundary of each CDR can be determined using any one or a combination of various well-known antibody CDR assignment systems including, e.g., Chothia based on the three-dimensional structure of antibodies and the topology of the CDR loops (Chothia et al., (1989) *Nature* 342:877-883; Al-Lazikani et al., Standard conformations for the canonical structures of immunoglobulins, *Journal of Molecular Biology,* 273:927-948 (1997)), Kabat based on antibody sequence variability (Kabat et al., Sequences of Proteins of Immunological Interest, $4^{th}$ Ed., U.S. Department of Health and Human Services, National Institutes of Health (1987)), AbM (University of Bath), Contact (University College London), International ImMunoGeneTics database (IMGT) (imgt.cines.fr/ on the World Wide Web), and North CDR definition based on the affinity propagation clustering using a large number of crystal structures. For example, according to different CDR determination schemes, the residues of each CDR are as follows.

| CDR | Kabat scheme | AbM scheme | Chothia scheme | Contact scheme |
|---|---|---|---|---|
| LCDR1 | L24-L34 | L24-L34 | L26-L32 | L30-L36 |
| LCDR2 | L50-L56 | L50-L56 | L50-L52 | L46-L55 |
| LCDR3 | L89-L97 | L89-L97 | L91-L96 | L89-L96 |
| HCDR1 | H31-H35B | H26-H35B | H26-H32 | H30-H35B |
| | | (Kabat numbering system) | | |
| | | | | |
| HCDR1 | H31-H35 | H26-H35 | H26-H32 | H30-H35 |
| | | (Chothia numbering system) | | |
| | | | | |
| HCDR2 | H50-H65 | H50-H58 | H53-H55 | H47-H58 |
| HCDR3 | H95-H102 | H95-H102 | H96-H101 | H93-H101 |
| | | (Kabat numbering system) | | |

Unless otherwise stated, the term "CDR" or "CDR sequence" used herein encompasses CDR sequences determined by any one of the schemes above. Those skilled in the art can readily determine the specific sequence of the CDRs based on the sequence of the variable region according to the rules described above.

A "conservative substitution" described herein refers to the replacement of an amino acid by another amino acid of the same class, e.g., the replacement of an acidic amino acid by another acidic amino acid, the replacement of a basic amino acid by another basic amino acid, or the replacement of a neutral amino acid by another neutral amino acid. Exemplary replacements are shown in the table below:

| Original residue | Exemplary replacement | Preferred conservative amino acid replacement |
|---|---|---|
| Ala (A) | Val, Leu, Ile | Val |
| Arg (R) | Lys, Gln, Asn | Lys |
| Asn (N) | Gln, His, Asp, Lys, Arg | Gln |
| Asp (D) | Glu, Asn | Glu |
| Cys (C) | Ser, Ala | Ser |
| Gln (Q) | Asn, Glu | Asn |
| Glu (E) | Asp, Gln | Asp |
| Gly (G) | Ala | Ala |
| His (H) | Asn, Gln, Lys, Arg | Arg |
| Ile (I) | Leu, Val, Met, Ala, Phe, Nle | Leu |
| Leu (L) | Nle, Ile, Val, Met, Ala, Phe | Ile |
| Lys (K) | Arg, Gln, Asn | Arg |

-continued

| Original residue | Exemplary replacement | Preferred conservative amino acid replacement |
|---|---|---|
| Met (M) | Leu, Phe, Ile | Leu |
| Phe (F) | Trp, Leu, Val, Ile, Ala, Tyr | Tyr |
| Pro (P) | Ala | Ala |
| Ser (S) | Thr | Thr |
| Thr (T) | Val, Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Nle | Leu |

Proteins Comprising Heterodimeric Fc

In one aspect, the present invention relates to a heterodimeric Fc scaffold that can be used to produce a heterodimeric Fc protein, such as a heterodimeric Fc fusion protein or a bispecific antibody. The heterodimeric Fc scaffold comprises a first Fc region comprising a first CH3 region and a second Fc region comprising a second CH3 region, wherein the first CH3 region and the second CH3 region are different in sequence, such that the heterodimeric interaction between the first CH3 region and the second CH3 region is stronger than the homodimeric interactions of the first CH3 region and the second CH3 region.

The heterodimeric Fc scaffold of the present invention can be linked to a target-binding domain in each of the first and second Fc regions to form a first target-binding region and a second target-binding region respectively, thus forming an Fc heterodimer. Therefore, the heterodimeric Fc scaffold of the present invention also encompasses such heterodimeric Fc scaffolds comprised in Fc heterodimers.

In another aspect, the present invention relates to a heterodimeric protein comprising the heterodimeric Fc scaffold, which is referred to as an "Fc heterodimer" herein.

In some embodiments, the Fc heterodimer of the present invention comprises a first target-binding region comprising a first Fc region comprising a first CH3 region, and a second target-binding region comprising a second Fc region comprising a second CH3 region, wherein the first CH3 region and the second CH3 region are different in sequence, such that the heterodimeric interaction between the first CH3 region and the second CH3 region is stronger than the homodimeric interactions of the first CH3 region and the second CH3 region.

In one embodiment, the target-binding region is selected from: (i) an antibody fragment, e.g., an antigen-binding fragment, comprising an Fc region, (ii) a fusion protein comprising an Fc region, e.g., an Fc region fused to a ligand, receptor, cytokine or hormone, and (iii) an Fc region conjugated to a prodrug, peptide, drug or toxin.

In one embodiment, the first and second target-binding regions are both antibody fragments comprising an Fc region. Thus, the Fc heterodimer of the present invention is a bispecific antibody.

In another embodiment, one of the first and second target-binding regions is an antibody fragment comprising an Fc region, while the other is a protein (e.g., a ligand or receptor) fused to an Fc, or the two target-binding regions are both proteins fused to an Fc. Thus, the heterodimer of the present invention is an Fc region fusion protein.

In some embodiments, the first CH3 region comprises an S364R/K (preferably S364R) mutation, and optionally one or more additional mutations. In some embodiments, the second CH3 region comprises a K370S/T/A/V (preferably K370S) mutation, and optionally one or more additional mutations. In some embodiments, the first CH3 region comprises an S364R/K mutation, and the second CH3 region comprises a K370S/T/A/V mutation. In some embodiments, the first CH3 region comprises an S364R mutation, and the second CH3 region comprises a K370S mutation.

In some embodiments, the first CH3 region comprises an S364R/K (preferably S364R) mutation and a D399K/R (preferably D399K) mutation. In some embodiments, the second CH3 region comprises a K370S/T/A/V (preferably K370S) mutation and a K409D/E (preferably K409D) mutation. In some embodiments, the first CH3 region comprises S364R/K+D399K/R, and the second CH3 region comprises K370S/T/A/V+Y349T/S/A/V. In some embodiments, the first CH3 region comprises S364R+D399K, and the second CH3 region comprises K370S+Y349T. In some embodiments, the first CH3 region further comprises E375N/Q (preferably E375N) and/or T350V/A (preferably T350V). In some embodiments, the second CH3 region further comprises K409D/E (preferably K409D), Q347D/E (preferably Q347D) and/or T350V/A (preferably T350V).

In some embodiments, the first CH3 region comprises S364R+D399K, and the second CH3 region comprises K370S+Y349T+K409D. In some embodiments, the first CH3 region further comprises E357N. In some embodiments, the second CH3 region further comprises Q347D. In some embodiments, the first CH3 region further comprises E357N, and the second CH3 region further comprises Q347D. In some embodiments, either of the first CH3 region or the second CH3 region further comprises T350V, or both comprise T350V.

Thus, in some embodiments, the first CH3 region comprises S364R+D399K, and the second CH3 region comprises K370S+Y349T+K409D+Q347D. In some embodiments, the first CH3 region comprises S364R+D399K+E357N, and the second CH3 region comprises K370S+Y349T+K409D+Q347D. In some embodiments, the first CH3 region comprises S364R+D399K+E357N+T350V, and the second CH3 region comprises K370S+Y349T+K409D+Q347D+T350V.

In some embodiments, the first CH3 region comprises K409E/D (preferably K409E). In some embodiments, the second CH3 region comprises D399K/R (preferably D399K) or K370T/S/A/V (preferably K370T). In some embodiments, the first CH3 region comprises K409E/D (preferably K409E) and the second CH3 region comprises D399K/R (preferably D399K). In some embodiments, the first CH3 region further comprises T411R/K (preferably T411R). In some embodiments, the second CH3 region further comprises K370T/S/A/V (preferably K370T). In some embodiments, the CH3 region comprises K409E/D+T411R/K, and the second CH3 region comprises D399K/R+K370T/S/A/V. In some embodiments, the CH3 region comprises K409E+T411R, and the second CH3 region comprises D399K+K370T.

In some specific embodiments, the first CH3 region and the second CH3 region have the following combinations of mutations:

| The first CH3 region | The second CH3 region |
| --- | --- |
| S364R, D399K, E357N, T350V | K370S, Y349T, Q347D, K409D, T350V |
| K409E, T411R | D399K, K370T |
| S364R, D399K, E357N | K370S, Y349T, Q347D, K409D |

-continued

| The first CH3 region | The second CH3 region |
| --- | --- |
| S364R, D399K | K370S, Y349T, Q347D, K409D |
| S364R, D399K | K370S, Y349T, K409D |

In some specific embodiments, the first CH3 region and the second CH3 region have mutations or combinations of mutations listed above compared to the parent CH3 region. In some specific embodiments, the first CH3 region and the second CH3 region differ from the parent CH3 region by mutations or combinations of mutations listed above. In some specific embodiments, the first CH3 region and the second CH3 region further comprise other mutations compared to the parent CH3 region, such as conservative mutations to other amino acids, or other mutations that arise as required by the Fc heterodimer.

In some embodiments, the first CH3 region and the second CH3 region comprise the following combinations:

(1) the first CH3 region comprises or consists of an amino acid sequence set forth in SEQ ID NO: 25, an amino acid sequence having 1-5 (e.g., 1, 2, 3, 4 or 5) mutations (preferably conservative substitutions) therefrom, or an amino acid sequence having at least 90%, 91%, 92%, 93%, 94%, 95%, 96%, 97%, 98% or 99% identity thereto; and the second CH3 region comprises or consists of the amino acid sequence set forth in SEQ ID NO: 28, an amino acid sequence having 1-5 (e.g. 1, 2, 3, 4 or 5) mutations (preferably conservative substitutions) therefrom, or an amino acid sequence having at least 90%, 91%, 92%, 93%, 94%, 95%, 96%, 97%, 98% or 99% identity thereto;

(2) the first CH3 region comprises or consists of an amino acid sequence set forth in SEQ ID NO: 29, an amino acid sequence having 1-5 (e.g., 1, 2, 3, 4 or 5) mutations (preferably conservative substitutions) therefrom, or an amino acid sequence having at least 90%, 91%, 92%, 93%, 94%, 95%, 96%, 97%, 98% or 99% identity thereto; and the second CH3 region comprises or consists of the amino acid sequence set forth in SEQ ID NO: 30, an amino acid sequence having 1-5 (e.g. 1, 2, 3, 4 or 5) mutations (preferably conservative substitutions) therefrom, or an amino acid sequence having at least 90%, 91%, 92%, 93%, 94%, 95%, 96%, 97%, 98% or 99% identity thereto;

(3) (3) the first CH3 region comprises or consists of an amino acid sequence set forth in SEQ ID NO: 32, an amino acid sequence having 1-5 (e.g., 1, 2, 3, 4 or 5) mutations (preferably conservative substitutions) therefrom, or an amino acid sequence having at least 90%, 91%, 92%, 93%, 94%, 95%, 96%, 97%, 98% or 99% identity thereto; and the second CH3 region comprises or consists of the amino acid sequence set forth in SEQ ID NO: 34, an amino acid sequence having 1-5 (e.g. 1, 2, 3, 4 or 5) mutations (preferably conservative substitutions) therefrom, or an amino acid sequence having at least 90%, 91%, 92%, 93%, 94%, 95%, 96%, 97%, 98% or 99% identity thereto;

(4) the first CH3 region comprises or consists of an amino acid sequence set forth in SEQ ID NO: 33, an amino acid sequence having 1-5 (e.g., 1, 2, 3, 4 or 5) mutations (preferably conservative substitutions) therefrom, or an amino acid sequence having at least 90%, 91%, 92%, 93%, 94%, 95%, 96%, 97%, 98% or 99% identity thereto; and the second CH3 region comprises or consists of the amino acid sequence set forth in SEQ ID NO: 34, an amino acid sequence having 1-5 (e.g. 1, 2, 3, 4 or 5) mutations (preferably conservative substitu-tions) therefrom, or an amino acid sequence having at least 90%, 91%, 92%, 93%, 94%, 95%, 96%, 97%, 98% or 99% identity thereto; and (5) the first CH3 region comprises or consists of an amino acid sequence set forth in SEQ ID NO: 33, an amino acid sequence having 1-5 (e.g., 1, 2, 3, 4 or 5) mutations (preferably conservative substitutions) therefrom, or an amino acid sequence having at least 90%, 91%, 92%, 93%, 94%, 95%, 96%, 97%, 98% or 99% identity thereto; and the second CH3 region comprises or consists of the amino acid sequence set forth in SEQ ID NO: 35, an amino acid sequence having 1-5 (e.g. 1, 2, 3, 4 or 5) mutations (preferably conservative substitu-tions) therefrom, or an amino acid sequence having at least 90%, 91%, 92%, 93%, 94%, 95%, 96%, 97%, 98% or 99% identity thereto.

In some specific embodiments, the first CH3 region and the second CH3 region comprise or consist of the following sequences:

| The first CH3 region | The second CH3 region |
| --- | --- |
| SEQ ID NO: 25 | SEQ ID NO: 28 |
| SEQ ID NO: 29 | SEQ ID NO: 30 |
| SEQ ID NO: 32 | SEQ ID NO: 34 |
| SEQ ID NO: 33 | SEQ ID NO: 34 |
| SEQ ID NO: 33 | SEQ ID NO: 35 |

In one embodiment, the first Fc region is an isotype selected from IgG1, IgG2, IgG3 and IgG4, and the second Fc region is an isotype selected from IgG1, IgG2, IgG3 and IgG4. In a preferred embodiment, the first Fc region and the second Fc region are both IgG1 isotypes or both IgG4 isotypes, or one is IgG1 isotype while the other one is IgG4 isotype.

In some embodiments, the parent Fc region or the parent CH3 region is from an IgG, for example, human IgG1, IgG2, IgG3 or IgG4 (e.g., wild-type human IgG1, IgG2, IgG3 or IgG4). In some embodiments, the parent Fc region or the parent CH3 region is from an IgG1, for example, wild-type human IgG1. In some embodiments, the parent Fc region comprises or consists of an amino acid sequence set forth in SEQ ID NO: 48, an amino acid sequence having 1-5 (e.g., 1, 2, 3, 4, or 5) mutations (preferably conservative substi-tutions) therefrom, or an amino acid sequence having at least 90%, 91%, 92%, 93%, 94%, 95%, 96%, 97%, 98% or 99% identity thereto.

In some embodiments, the parent CH3 region comprises or consists of an amino acid sequence set forth in SEQ ID NO: 49, an amino acid sequence having 1-5 (e.g., 1, 2, 3, 4, or 5) mutations (preferably conservative substitutions) therefrom, or an amino acid sequence having at least 90%, 91%, 92%, 93%, 94%, 95%, 96%, 97%, 98% or 99% identity thereto.

In some embodiments, the Fc region comprises a CH2 comprising or consisting of an amino acid sequence set forth in SEQ ID NO: 24, an amino acid sequence having 1-5 (e.g., 1, 2, 3, 4, or 5) mutations (preferably conservative substi-tutions) therefrom, or an amino acid sequence having at least 90%, 91%, 92%, 93%, 94%, 95%, 96%, 97%, 98% or 99% identity thereto.

In some specific embodiments, the first Fc region consists of a CH2 and a first CH3 region, and the second Fc region consists of a CH2 and a second CH3 region.

In some embodiments, the target-binding region can bind to an antigen or a receptor. In some embodiments, the antigen is selected from PD1, PDL1, PDL2, CD20, CD47, HER2 or GPC3. In some embodiments, the receptor is IL-2R.

In some embodiments, the target-binding region may be an antigen-binding fragment, e.g., Fab, VH region (VHH) or scFv, linked to an Fc region. In some embodiments, the target-binding region may be a ligand, e.g., IL-2, linked to an Fc region.

In some embodiments, the antigen-binding fragment or ligand is linked to the Fc region by a linker or hinge region comprising, for example, SEQ ID NO: 23, 27, 38 or 40.

In some embodiments, the target-binding region com-prises IL-2 or a mutant protein thereof from, e.g., Chinese Patent Application No. 202010197740.4, preferably com-prising an amino acid sequence set forth in SEQ ID NO: 26, an amino acid sequence having 1-5 (e.g., 1, 2, 3, 4, or 5) mutations (preferably conservative substitutions) therefrom, or an amino acid sequence having at least 85%, 90%, 91%, 92%, 93%, 94%, 95%, 96%, 97%, 98% or 99% identity thereto.

In some embodiments, the target-binding region com-prises an antigen-binding fragment from, e.g., the anti-PD1 antibody from WO2017024465A1, the anti-CD20 antibody Rituxan, the anti-GPC3 antibody from U.S. Pat. No. 7,979, 086B2 or anti-Her2 antibody pertuzumab. In some embodi-ments, the antigen-binding fragment comprises 3 CDRs from a heavy chain variable region VH, and/or 3 CDRs from a light chain variable region. In some embodiments, the antigen-binding fragment comprises a heavy chain variable region VH and/or a light chain variable region VL.

In some embodiments, the antigen-binding fragment spe-cifically binds to PD1, wherein the VH comprises or consists of an amino acid sequence set forth in SEQ ID NO: 21, or an amino acid sequence having at least 90%, 91%, 92%, 93%, 94%, 95%, 96%, 97%, 98% or 99% identity to the amino acid sequence; and/or the VL comprises or consists of an amino acid sequence set forth in SEQ ID NO: 42, or an amino acid sequence having at least 90%, 91%, 92%, 93%, 94%, 95%, 96%, 97%, 98% or 99% identity to the amino acid sequence; preferably, the antigen-binding fragment is an Fab fragment. In some embodiments, the antigen-binding fragment comprises 3 CDRs from a heavy chain variable region VH set forth in SEQ ID NO: 21, and/or 3 CDRs from a light chain variable region set forth in SEQ ID NO: 42.

In some embodiments, the antigen-binding fragment spe-cifically binds to CD20, wherein the VH comprises or consists of an amino acid sequence set forth in SEQ ID NO: 31, or an amino acid sequence having at least 90%, 91%, 92%, 93%, 94%, 95%, 96%, 97%, 98% or 99% identity to the amino acid sequence; and/or the VL comprises or consists of an amino acid sequence set forth in SEQ ID NO: 45, or an amino acid sequence having at least 90%, 91%, 92%, 93%, 94%, 95%, 96%, 97%, 98% or 99% identity to the amino acid sequence; preferably, the antigen-binding fragment is an Fab fragment. In some embodiments, the antigen-binding fragment comprises 3 CDRs from a heavy chain variable region VH set forth in SEQ ID NO: 31, and/or 3 CDRs from a light chain variable region set forth in SEQ ID NO: 45.

In some embodiments, the antigen-binding fragment spe-cifically binds to GPC3, wherein the VH comprises or consists of an amino acid sequence set forth in SEQ ID NO: 36, or an amino acid sequence having at least 90%, 91%, 92%, 93%, 94%, 95%, 96%, 97%, 98% or 99% identity to the amino acid sequence; and/or the VL comprises or consists of an amino acid sequence set forth in SEQ ID NO: 46, or an amino acid sequence having at least 90%, 91%, 92%, 93%, 94%, 95%, 96%, 97%, 98% or 99% identity to the amino acid sequence; preferably, the antigen-binding fragment is an Fab fragment. In some embodiments, the antigen-binding fragment comprises 3 CDRs from a heavy chain variable region VH set forth in SEQ ID NO: 36, and/or 3 CDRs from a light chain variable region set forth in SEQ ID NO: 46.

In some embodiments, the antigen-binding fragment specifically binds to HER2, wherein the VH comprises or consists of an amino acid sequence set forth in SEQ ID NO: 41, or an amino acid sequence having at least 90%, 91%, 92%, 93%, 94%, 95%, 96%, 97%, 98% or 99% identity to the amino acid sequence; and/or the VL comprises or consists of an amino acid sequence set forth in SEQ ID NO: 44, or an amino acid sequence having at least 90%, 91%, 92%, 93%, 94%, 95%, 96%, 97%, 98% or 99% identity to the amino acid sequence; preferably, the antigen-binding fragment is an Fab fragment. In some embodiments, the antigen-binding fragment comprises 3 HCDRs from a heavy chain variable region VH set forth in SEQ ID NO: 41, and/or 3 LCDRs from a light chain variable region set forth in SEQ ID NO: 44.

In some embodiments, the antigen-binding fragment specifically binds to PDL1, wherein preferably the antigen-binding fragment is a VH region or VHH, e.g., comprising or consisting of an amino acid sequence set forth in SEQ ID NO: 37, or an amino acid sequence having at least 90%, 91%, 92%, 93%, 94%, 95%, 96%, 97%, 98% or 99% identity to the amino acid sequence. In some embodiments, the antigen-binding fragment comprises 3 HCDRs in a VHH set forth in SEQ ID NO: 37.

In some embodiments, the antigen-binding fragment specifically binds to CD47, wherein preferably the antigen-binding fragment is an scFv, e.g., comprising or consisting of an amino acid sequence set forth in SEQ ID NO: 39, or an amino acid sequence having at least 90%, 91%, 92%, 93%, 94%, 95%, 96%, 97%, 98% or 99% identity to the amino acid sequence. In some embodiments, the antigen-binding fragment comprises 3 HCDRs and/or 3 LCDRs comprised in an scFv set forth in SEQ ID NO: 39.

In some embodiments, the Fc heterodimers of the present invention have the following configuration:

the first/second target-binding region comprises an Fab fragment derived from an antibody and the first/second Fc region linked thereto, the second/first target-binding region comprises a ligand and the second/first Fc region linked thereto;

the first/second target-binding region comprises an Fab fragment derived from an antibody and the first/second Fc region linked thereto, the second/first target-binding region comprises an scFv derived from an antibody and the second/first Fc region linked thereto;

the first/second target-binding region comprises an Fab fragment derived from an antibody and the first/second Fc region linked thereto, the second/first target-binding region comprises a VHH derived from an antibody and the second/first Fc region linked thereto; or the first/second target-binding region comprises an Fab fragment derived from an antibody and the first/second Fc region linked thereto, the second/first target-binding region comprises an Fab fragment derived from an antibody and the second/first Fc region linked thereto.

Preparation of Proteins Comprising Heterodimeric Fc

The present invention further provides a method for producing an Fc heterodimer in vitro. In some embodiments, the Fc heterodimer is a bispecific antibody or an Fc region fusion protein.

In a first aspect, the present invention relates to a method for producing Fc heterodimers in vitro, comprising:

a) providing the first target-binding region comprising the first Fc region comprising the first CH3 region, b) providing the second target-binding region comprising the second Fc region comprising the second CH3 region, wherein the first CH3 region and the second CH3 region are different in sequence, such that the heterodimeric interaction between the first CH3 region and the second CH3 region is stronger than the homodimeric interactions of the first CH3 region and the second CH3 region, c) assembling the first target-binding region and the second target-binding region, and d) obtaining the Fc heterodimer.

In some embodiments, the target-binding region, the Fc region or the CH3 region is as defined above.

In a preferred aspect, the first target-binding region and the second target-binding region are not mirror images of each other in structure (i.e., the two target-binding regions are different in structure). For example, one target-binding region is an Fab linked to an Fc region and the other target-binding region is a VHH, scFv, ligand or other polypeptide linked to an Fc region. In another preferred aspect, the first target-binding region and the second target-binding region are mirror images of each other in structure (i.e., the structures of the two target-binding regions are identical). For example, both comprise an Fab linked to an Fc region.

In a preferred aspect, for example, when the first target-binding region and the second target-binding region are not mirror images of each other in structure, Step c) comprises:

c1) introducing nucleic acids encoding chains of the first target-binding region and nucleic acids encoding chains of the second target-binding region into a host cell;

c2) expressing and assembling the first target-binding region and the second target-binding region in the host cell.

In another preferred aspect, for example, when the first target-binding region and the second target-binding region are mirror images of each other in structure, Step c) comprises:

c1) introducing nucleic acids encoding chains of the first target-binding region into a host cell;

c2) expressing and assembling the first target-binding region in the host cell, and optionally purifying the first target-binding region;

c3) introducing nucleic acids encoding chains of the second target-binding region into the host cell;

c4) expressing and assembling the second target-binding region in the host cell, and optionally purifying the second target-binding region; and c5) assembling the first target-binding region and the second target-binding region in vitro.

In yet another embodiment, a compound, such as L-arginine, is added to the culture medium during antibody production. In one embodiment, the arginine is used to stabilize the protein.

In one embodiment, the first and/or second target-binding region is conjugated to a drug, prodrug or toxin, or comprises a receptor group for a drug, prodrug or toxin. Such receptor group may be, for example, a non-natural amino acid.

In one embodiment, the increased strength of the heterodimeric interaction as compared to various homodimeric interactions is due to the mutations in the CH3 region described herein.

In some embodiments, the product of the present invention has similar or comparable thermal stability to homodimers.

In some embodiments, the method of the present invention produces stable heterodimeric proteins in high yield.

In some embodiments, the sequences of the first CH3 region and the second CH3 region comprise amino acid mutations (substitutions) at positions that are not completely identical. In some embodiments, the sequences of the first CH3 region and the second CH3 region comprise amino acid mutations (substitutions) at positions that are completely different. The amino acid substituent may be a natural amino acid.

In some embodiments, the Fc heterodimer of the present invention is produced by a reduction reaction and a subsequent oxidation reaction between the first and second target-binding regions. In some embodiments, the Fc heterodimer of the present invention is formed by connection via one or more disulfide bonds. In some embodiments, the first target-binding region and the second target-binding region of the present invention are associated due to mutations in the CH3 region. Generally, the association is a covalent bond in physiological conditions. Preferably, due to mutations in the CH3 region, the formation of homodimers of the first target-binding region and the second target-binding region of the present invention is inhibited in reducing conditions (which would support homodimer pairing by non-covalent bonds in the absence of said mutation), while the association of heterodimer is promoted in such reducing conditions. The "association of heterodimer" generally refers to covalent binding interactions, and sometimes also includes non-covalent binding interactions (e.g., hydrophobic interaction or hydrogen bonding interaction).

In some embodiments, one or both of the first target-binding region or the second target-binding region is a "half antibody" or "half molecule", which refers to an antibody fragment containing only the "half" of an intact immunoglobulin heterotetramer that generally comprises one heavy chain of an antibody and one light chain of an antibody. For example, the heavy chain and light chain of the half-antibody are bound by covalent or non-covalent interactions such as hydrophobic interactions or hydrogen bonds. In one embodiment, the half antibody is generally monovalent and comprises a mutant CH3 region (e.g., the mutant CH3 region of the present invention, as described above). In a preferred embodiment, the Fc heterodimer of the present invention comprises two half antibodies that bind to different antigens.

Nucleic Acids and Host Cells

The present invention further relates to nucleic acids encoding the regions/chains of the target-binding regions of the Fc heterodimer described herein. In one embodiment, the present invention relates to a nucleic acid encoding an amino acid sequence of a region/chain set forth in the Sequence Listing.

In one embodiment, one or more vectors comprising the nucleic acid are provided. In one embodiment, the vector is an expression vector, such as a eukaryotic expression vector. The vector includes, but is not limited to, a virus, a plasmid, a cosmid, a phage, or a yeast artificial chromosome (YAC). In one embodiment, the vector is pTT5 vector or pcDNA3.1.

In one embodiment, a host cell comprising the nucleic acid or the vector is provided. Suitable host cells for cloning or expressing the nucleic acid encoding the region/chain of the target-binding region of the Fc heterodimer of the present invention or the vector comprising the same include prokaryotic or eukaryotic cells. In one embodiment, the host cell is prokaryotic. In another embodiment, the host cell is eukaryotic. In another embodiment, the host cell is selected from a yeast cell, a mammalian cell, and other cells suitable for preparing an antibody or an antigen-binding fragment thereof. For example, eukaryotic microorganisms, such as filamentous fungi or yeast, are suitable cloning or expressing hosts for the vector encoding the antibody. For example, fungus and yeast strains in which the glycosylation pathway has been "humanized" may produce antibodies having a partial or full human glycosylation pattern. See Gerngross, Nat. Biotech., 22:1409-1414 (2004), and Li et al., Nat. Biotech., 24:210-215 (2006). Host cells suitable for expressing glycosylated antibodies are also derived from multicellular organisms (invertebrates and vertebrates). Vertebrate cells may also be used as hosts. For example, a mammalian cell line engineered to be suitable for suspension growth may be used. Other examples of useful mammalian host cell lines are monkey kidney CV1 cell line (COS-7) transformed with SV40, human embryonic kidney cell lines (293HEK or 293F or 293 cells, as described in, e.g., Graham et al., J. Gen Virol., 36:59 (1977)) and the like. Other useful mammalian host cell lines include Chinese hamster ovary (CHO) cells, including DHFR-CHO cells (Urlaub et al., Proc. Natl. Acad. Sci. USA 77:216 (1980)), CHO-S cells, ExpiCHO and the like; and myeloma cell lines such as Y0, NS0, and Sp2/0. For reviews of certain mammalian host cell lines suitable for antibody production, see, for example, Yazaki and Wu, Methods in Molecular Biology, Vol. 248 (B. K. C. Lo, Ed., Humana Press, Totowa, NJ), pg. 255-268 (2003). In preferred embodiments, the host cell is selected from a yeast cell, a mammalian cell (e.g., a CHO cell (e.g., CHO-S or ExpiCHO) or 293 cell (e.g., Expi293 cell, HEK293 cell, 293F cell, etc.)) or other cells suitable for preparing an antibody or an antigen-binding fragment thereof.

The present invention further relates to compositions (e.g., pharmaceutical compositions) comprising the Fc heterodimers, methods of treating diseases, such as cancer, using the Fc heterodimers, or uses for such treatment.

EXAMPLES

Example 1. Design of Heterodimeric Fc Scaffolds Based on Antibody CH3 and Fc Heterodimers Comprising the Same A monoclonal antibody consists of two heavy chains and two light chains. One of the heavy chains and one of the light chains form a heterodimer, and the two heavy chains form a homodimer, as shown in FIG. 1. The heavy chain comprises 4 domains, VH, CH1, CH2 and CH3. VH and CH1 respectively form heterodimers with VL and CL of the light chain, and CH2 and CH3 form a homodimer. Among these, CH3 has the highest homodimeric binding energy with a Tm>80° C. Thus, altering amino acids responsible for the interaction at the contact interface of CH3 may prevent the homodimerization of CH3 and facilitate the heterodimerization of CH3 by introducing new pairs of action.

Figure 2:
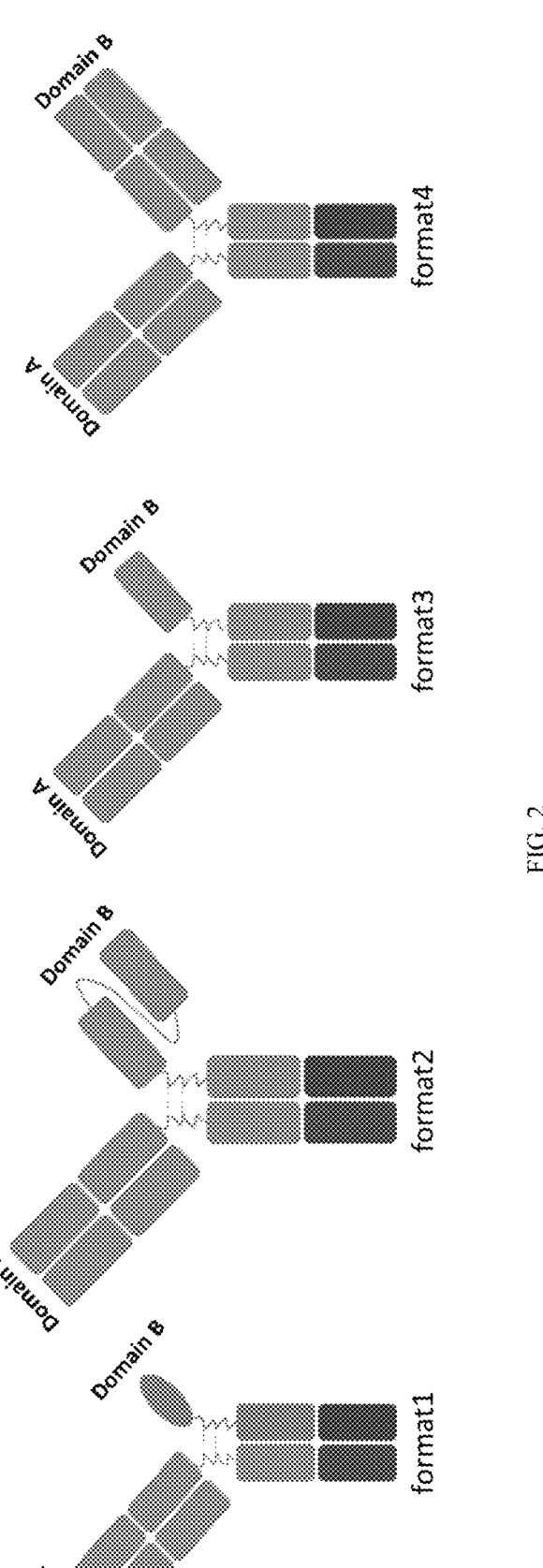
FIG. 2 shows the configurations of Fc heterodimers according to the present invention.

The interfacial amino acids and the interacting amino acids of CH3 homodimers are listed in Table 1. CH3-mutant heavy chains based on steric hindrance and electrostatic repulsion were designed to prevent homodimerization by, for example, forming a pair of salt bridges between D399 and K409' on the CH3 homodimeric interface. The K409'D mutation damages the original salt bridges and forms electrostatic repulsion between D399 and D409' on the homodimeric interface. The introduction of amino acids with large side chains such as L368Y, K409W and T411R on the homodimerization interface also reduces the homodimerization through steric hindrance. The design of the other heavy chain is based on spatial complementation, opposite-charge mutation and salt bridge introduction to enhance the formation of the heterodimer. For example, D399K is the complementary charge mutation introduced based on K409'D, and K370S and F405T are the mutations introduced based on spatial complementation. Based on the crystal structure of the interface of CH3, the original interfacial interaction is changed, and the interface is reconstructed to reduce the homodimerization of molecules and enhance the heterodimerization. Mutation combinations are listed in Table 2. The formats of bispecific molecules are shown in FIG. 2.

TABLE 1

Amino acids with interactions at the antibody CH3 interface
Amino acids at antibody CH3 interface (PDB: 4W4N, amino
acid sequence numbered as per EU numbering scheme)

| Chain A | Contacting Residues in Chain B |
|---|---|
| GLN A 347 | LYS B 360' |
| TYR A 349 | SER B 354', ASP B 356', GLU B 357', LYS B 360' |
| THR A 350 | SER B 354', ARG B 355' |
| LEU A 351 | LEU B 351', PRO B 352', PRO B 353', SER B 354', THR B 366' |
| SER A 354 | TYR B 349', THR B 350', LEU B 351' |
| ARG A 355b | THR B 350' |
| ASP A 356 | TYR B 349', LYS B 439' |
| GLU A 357 | TYR B 349', LYS B 370' |
| LYS A 360b | GLN B 347', TYR B 349' |
| SER A 364 | LEU B 368', LYS B 370' |
| THR A 366 | LEU B 351', TYR B 407' |

TABLE 1-continued

Amino acids with interactions at the antibody CH3 interface
Amino acids at antibody CH3 interface (PDB: 4W4N, amino
acid sequence numbered as per EU numbering scheme)

| Chain A | Contacting Residues in Chain B |
|---|---|
| LEU A 368 | SER B 364', LYS B 409' |
| LYS A 370 | GLU B 357', SER B 364' |
| ASN A 390 | SER B 400' |
| LYS A 392 | LEU B 398', ASP B 399', SER B 400', PHE B 405' |
| THR A 394 | THR B 394', VAL B 397', PHE B 405', TYR B 407' |
| PRO A 395 | VAL B 397' |
| VAL A 397 | THR B 393', THR B 394', PRO B 395' |
| ASP A 399 | LYS B 392', LYS B 409' |
| SER A 400 | ASN B 390', LYS B 392' |
| PHE A 405 | LYS B 392', THR B 394', LYS B 409' |
| TYR A 407 | THR B 366', THR B 394', TYR B 407', SER B 408', LYS B 409' |
| LYS A 409 | LEU B 368', ASP B 399', PHE B 405', TYR B 407' |
| LYS A 439 | ASP B 356' |

TABLE 2

Mutation combination design of CH3 interfacial amino acids

| Heterodimeric Fc scaffold ID | Domain A-Fc mutation (Fc-A mutation) | Domain B-Fc mutation (Fc-B mutation) |
|---|---|---|
| HD-001 | S364R, D399K, E357N, T350V | K370S, Y349T, Q347D, K409D, T350V |
| HD-002 | K409E, T411R | D399K, K370T |
| HD-003 | S364R, D399K, E357N | K370S, Y349T, Q347D, K409D |
| HD-004 | S364R, D399K | K370S, Y349T, Q347D, K409D |
| HD-005 | S364R, D399K | K370S, Y349T, K409D |

TABLE A

Information of Fc heterodimer molecule constructs

| Fc heterodimer molecule ID | Heterodimeric Fc scaffold ID | Format | Domain A* (first target-binding region; comprising Fc region) | Domain B* (second target-binding region; comprising Fc region) | Mutations in Fc-A | Mutations in Fc-B |
|---|---|---|---|---|---|---|
| HDM-001 | HD-001 | format1 | Half-antibody of anti-PD1 antibody (from WO2017024465A1) HC: SEQ ID NO: 1; LC: SEQ ID NO: 17 | IL-2 mutant + Fc region SEQ ID NO: 2 | S364R, D399K, E357N, T350V | K370S, Y349T, Q347D, K409D, T350V |
| HDM-002 | HD-002 | format1 | Half-antibody of anti-PD1 antibody (from WO2017024465A1) HC: SEQ ID NO: 3; LC: SEQ ID NO: 17 | IL-2 mutant + Fc region SEQ ID NO: 4 | K409E, T411R | D399K, K370T |
| HDM-003 | HD-003 | format1 | Half-antibody of anti-PD1 antibody (from WO2017024465A1) HC: SEQ ID NO: 6; LC: SEQ ID NO: 17 | IL-2 mutant + Fc region SEQ ID NO: 8 | S364R, D399K, E357N | K370S, Y349T, Q347D, K409D |
| HDM-004 | HD-004 | format1 | Half-antibody of anti-PD1 antibody (from WO2017024465A1) HC: SEQ ID NO: 7; LC: SEQ ID NO: 17 | IL-2 mutant + Fc region SEQ ID NO: 8 | S364R, D399K | K370S, Y349T, Q347D, K409D |
| HDM-005 | HD-005 | format1 | Half-antibody of anti-PD1 antibody (from WO2017024465A1) HC: SEQ ID NO: 7; LC: SEQ ID NO: 17 | IL-2 mutant + Fc region SEQ ID NO: 9 | S364R, D399K | K370S, Y349T, K409D |
| HDM-006 | HD-005 | format1 | Half-antibody of anti-PD1 antibody (from WO2017024465A1) HC: SEQ ID NO: 10; LC: SEQ ID NO: 19 | IL-2 mutant + Fc region SEQ ID NO: 9 | S364R, D399K | K370S, Y349T, K409D |
| HDM-007 | HD-005 | format2 | Half-antibody of anti-CD20 antibody (Rituxan) HC: SEQ ID NO: 20; LC: SEQ ID NO: 19 | Anti-CD47 scFv (from CN109422811A) + Fc region SEQ ID NO: 15 | S364R, D399K | K370S, Y349T, K409D |

TABLE A-continued

Information of Fc heterodimer molecule constructs

| Fc heterodimer molecule ID | Heterodimeric Fc scaffold ID | Format | Domain A* (first target-binding region; comprising Fc region) | Domain B* (second target-binding region; comprising Fc region) | Mutations in Fc-A | Mutations in Fc-B |
|---|---|---|---|---|---|---|
| HDM-008 | HD-005 | format2 | Half-antibody of anti-GPC3 antibody (from U.S. Pat. No. 7,979,086B2) HC: SEQ ID NO: 11; LC: SEQ ID NO: 20 | Anti-CD47 scFv (from CN109422811A) + Fc region SEQ ID NO: 15 | S364R, D399K | K370S, Y349T, K409D |
| HDM-009 | HD-005 | format3 | Half-antibody of anti-CD20 antibody (Rituxan) HC: SEQ ID NO: 10; LC: SEQ ID NO: 19 | Anti-PDL1 VHH (from CN109970860A) + Fc region SEQ ID NO: 13 | S364R, D399K | K370S, Y349T, K409D |
| HDM-010 | HD-001 | format4 | Half-antibody of anti-PD1 antibody (from WO2017024465A1) HC: SEQ ID NO: 1; LC: SEQ ID NO: 17 | Half-antibody of anti-CD20 antibody (Rituxan) HC: SEQ ID NO: 5; LC: SEQ ID NO: 19 | S364R, D399K, E357N, T350V | K370S, Y349T, Q347D, K409D, T350V |
| HDM-011 | HD-005 | format4 | Half-antibody of anti-PD1 antibody (from WO2017024465A1) HC: SEQ ID NO: 7; LC: SEQ ID NO: 17 | Half-antibody of anti-CD20 antibody (Rituxan) HC: SEQ ID NO: 14; LC: SEQ ID NO: 19 | S364R, D399K | K370S, Y349T, K409D |
| HDM-012 | HD-005 | format4 | Half-antibody of anti-HER2 antibody (pertuzumab) HC: SEQ ID NO: 16; LC: SEQ ID NO: 18 | Half-antibody of anti-PD1 antibody (from WO2017024465A1) HC: SEQ ID NO: 12; LC: SEQ ID NO: 17 | S364R, D399K | K370S, Y349T, K409D |

*See the Sequence Listing for SEQ ID NOs and sequence information for various domains in Domain A and Domain B.

Example 2. Expression and Purification of Fc Heterodimers

Fc heterodimer molecules, HDM001-HDM005, of Format 1 in FIG. 2 were constructed. For the specific sequence information, see Table A and the Sequence Listing.

Plasmid construction: The sequences of chains of the above-mentioned Domain A and Domain B were synthesized by Genewiz, and the Domain A sequences were cloned into pcDNA3.1 to give plasmids.

Expression and Purification of Proteins

Preparation of transient plasmids: 1/10 (based on the transfection volume) of Opti MEM (Gibco, Catalog No. 31985-070) was added to the above plasmids (50 μg/50 mL, mass ratio of the three chains=1:1:1). The Opti-MEM medium containing plasmids was filtered into a new 50-mL centrifuge tube, and filtered PEI (1 g/L, Polysciences) was added to the centrifugal tube (mass ratio of plasmid to PEI=1:3). The mixture was mixed well and let stand for 20 mM.

Cell transfection: The DNA/PEI mixture was poured gently to Expi293 cells (Gibco) and mixed well. The cells were incubated at 37° C./8% $CO_2$. 14 h after transfection, VPA (2.2 M, Sigma), 2.5% glucose (200 g/L, Sigma) and 2.5% Feed (1 g/L Phytone peptone+1 g/L Difco Select Phytone) were added at 0.1% of the volume of transfected cells, and the cells were incubated at 37° C./8% $CO_2$.

The obtained cell culture broth was centrifuged at 4000 rpm for 50 mM, and the supernatant was collected and purified by a pre-packed column Hitrap Mabselect Sure (GE, 11-0034-95). As per the product instruction, the procedures are as follows: The packed column was equilibrated with 5 column volumes of equilibration buffer (20 mM Tris, 150 mM NaCl, pH 7.2) before purification; the collected supernatant was loaded on the column, and then the column was washed with 10 column volumes of equilibration buffer to remove non-specific binding proteins; and the column was washed with 5 column volumes of eluent buffer (100 mM sodium citrate, pH 3.5), and the eluate was collected. The eluate was adjusted to pH 6.0 with 2 M Tris and the concentration was measured to give purified molecular products. The yields are given in Table 3.

Figure 3:
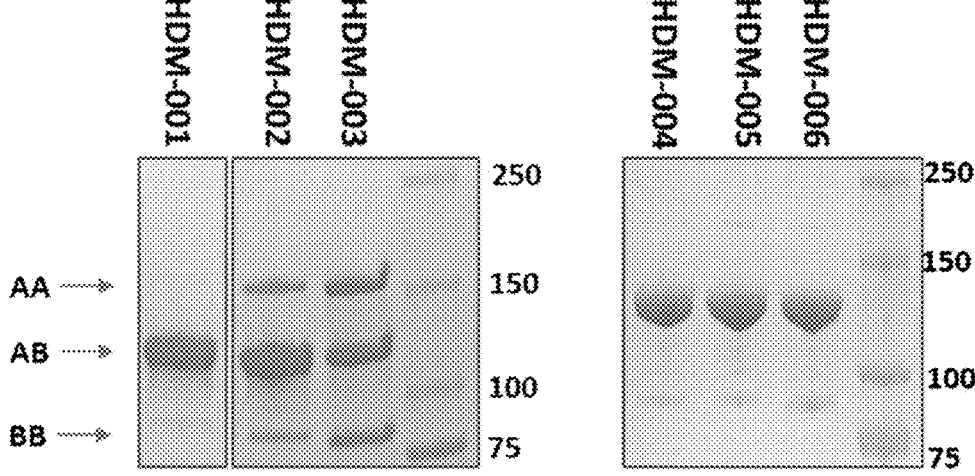
FIG. 3 shows non-reducing SDS-PAGE of the Fc heterodimers.

Product Purity Analysis by SDS-PAGE:

5 μg of protein A affinity purification product obtained by Hitrap Mabselect Sure column purification was detected for the relative contents of homodimers and heterodimer in non-reduced conditions by SDS-PAGE electrophoresis, and the proportion of each protein band in the gel electrophoresis image was analyzed by ImageLab (BioRad) software. The results are shown in FIG. 3 and Table 3. The proportions of heterodimers HDM-001, HDM-003, HDM-004 and HDM-005 were greater than 85%, and the yields of molecules were greater than 100 mg/L and were greater than that of HDM-002 mutant combination.

TABLE 3

Yield and heterodimer proportion of the molecules

| Molecule | Yield (mg/L) | Heterodimer proportion |
|---|---|---|
| HDM-001 | 115.8 | 88.70% |
| HDM-002 | 67.8 | 66.20% |
| HDM-003 | 117.4 | 91.80% |
| HDM-004 | 131.5 | 91.30% |
| HDM-005 | 130 | 87.60% |

Example 3. Versatility Validation of Heterodimeric Fc Scaffolds

In order to verify the versatility of the heterodimeric Fc scaffold HD-005 in different sequences and molecular formats, molecules of Format 2 and Format 3 as shown in FIG. 2, HDM-006 to HDM-009, were constructed. The molecule and sequence information is shown in Table A and the Sequence Listing. The preparation method is the same as in Example 2.

Figure 4:
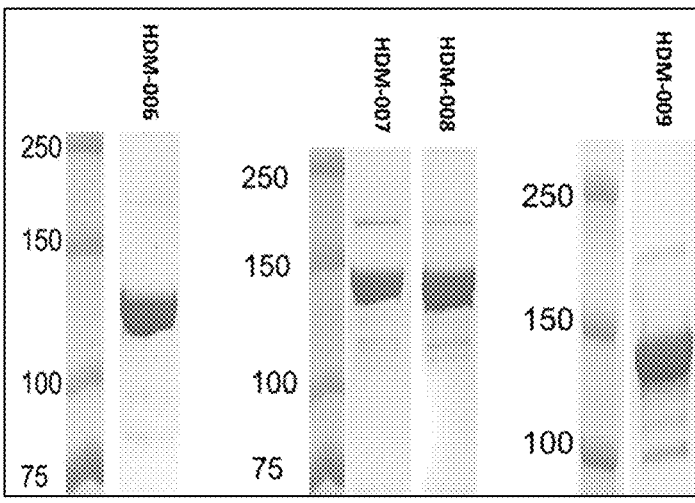
FIG. 4 shows non-reducing SDS-PAGE of the Fc heterodimers.

As can be seen from the results in FIG. 4 and table 4, the proportions of the Fc heterodimers obtained were 85% or higher, although the sequences and the molecular formats were different.

TABLE 4

| Yield and heterodimer proportion of the molecules | | |
|---|---|---|
| Molecule | Yield (mg/L) | Heterodimer proportion |
| HDM-006 | 546 | 94% |
| HDM-007 | 364 | 90.2% |
| HDM-008 | 238 | 94.6% |
| HDM-009 | 150 | 88.1% |

Example 4. In Vitro Assembly of Fc Heterodimers

To investigate the formation of Fc heterodimers of Format 4 (FIG. 2) from the heterodimeric Fc scaffold obtained in this study, molecules of Format 4 were constructed. The Fc heterodimers of Format 4 differ from those of formats 1-3 in that two Fab fragments binding different antigens are linked to Fc, and the molecule is composed of 2 heavy chains and 2 light chains. To prevent the wrong pairing combination, the mutation combinations in Example 1 were introduced in CH3 of the two heavy chains to prevent the heavy chain from mismatching, while the correct pairing of the light chains was achieved by the in vitro assembly of the molecules. The information of HDM-010, HDM-011 and HDM-012 is shown in Table A and the Sequence Listing.

Figure 5:
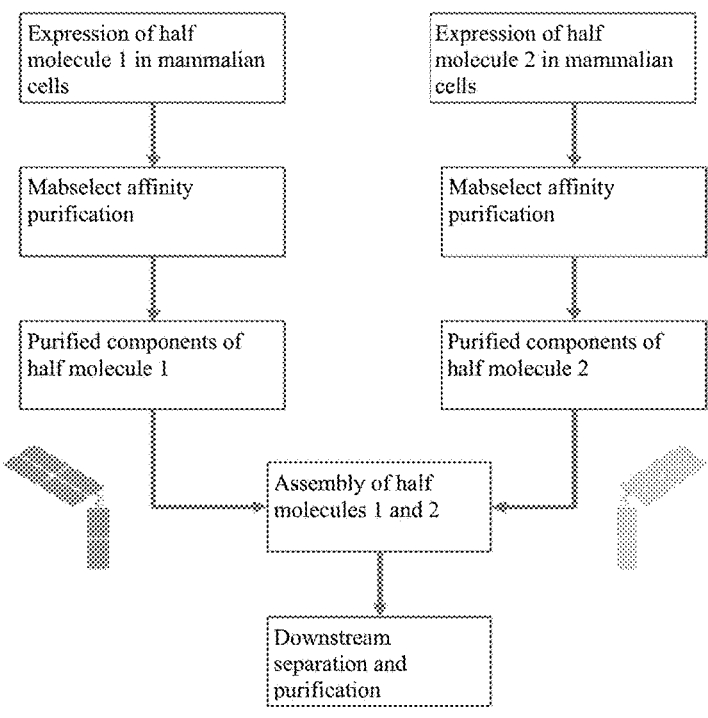
FIG. 5 shows the preparation pathway of the Fc heterodimers.

The specific preparation route is shown in FIG. 5. Half molecule 1 (half antibody 1) and half molecule 2 (half antibody 2) were prepared separately and then incubated in redox conditions to form Fc heterodimers. This study investigated the effect of different redox conditions on the production of bispecific molecules.

Preparation of Half Molecules:

Plasmid construction: The light and heavy chain sequences of the half molecules were synthesized by the Genewiz and cloned into vector pcDNA3.1 to give plasmids containing the light and heavy chain genes. The plasmids were then transfected into ExpiCHO cells (Gibco).

Transient Expression in ExpiCHO Cells:

Transient plasmid preparation: 8% (v/v) of the final volume of OptiPRO™ SFM (Gibco, Catalog No. 12309-019) was used as the transfection buffer and added to the light chain plasmid and heavy chain plasmid of the half molecules (0.8 μg/mL cells, the mass ratio of the light chain plasmid and heavy chain plasmid of the half molecules=1:1). The mixture was mixed well and filtered through a 0.22 μm filter for sterilization. The transfection reagent in Expi-Fectamine™ CHO Transfection Kit (Gibco, Catalog No. A29130) was added at 3.2 μL/mL, and complexes of the transfection reagent and plasmid DNA were incubated at room temperature for 1-5 min to give transient plasmids.

Cell transfection: On the day of transfection, the cell density was adjusted to $6 \times 10^6$ cells/mL using ExpiCHO™ Expression Medium (Gibco, Catalog No. A29100-01). The prepared transient plasmid complexes were added to ExpiCHO cells (Gibco). The cells were incubated at 37° C./8% $CO_2$ for 18 h, and incubated for 6 days after addition of 0.6% (v/v) of Enhancer (Gibco, ExpiFectamine CHO Enhancer) and 30% (v/v) of Feed (Gibco, A29101-01).

Purification of half-molecule products: The obtained cell culture broth was centrifuged at 4000 rpm for 50 mM, and the supernatant was collected and purified by a pre-packed column Hitrap Mabselect Sure (GE, 11-0034-95). As per the product instruction, the procedures are as follows: The packed column was equilibrated with 5 column volumes of equilibration buffer (20 mM Tris, 150 mM NaCl, pH 7.2) before purification; the collected supernatant was loaded on the column, and then the column was washed with 10 column volumes of equilibration buffer to remove non-specific binding proteins; the column was washed with 5 column volumes of eluent buffer (100 mM sodium citrate, pH 3.5), and the eluate was collected. The eluate was adjusted to pH 6.0 with 2 M Tris and the concentration was measured. 100 μg of purified protein sample was detected for protein purity using a gel filtration chromatographic column SW3000 (TOSOH, Catalog No. 18675) and purified half molecule products were obtained. The parameters are shown in Table 5 below.

TABLE 5

| Yield of half molecules | |
|---|---|
| Molecule* | Yield (mg/L) |
| HD-2001 (HDM010-domain A) | 200 |
| HD-2002 (HDM010-domain B) | 300 |
| HD-2003 (HDM011-domain A) | 147 |
| HD-2004 (HDM011-domain B) | 360 |
| HD-2005 (HDM012-domain A) | 116 |
| HD-2006 (HDM012-domain B) | 374 |

*The sequence information is shown in Table A and the Sequence Listing

Preparation of Fc Heterodimers HDM010, 011 and 012:

1) Collected solutions of corresponding half molecules obtained by affinity chromatography as shown in Table 6 below were mixed in a molar ratio of 1:1. 10 mM GSH (Sigma-Aldrich, G4251-100G) was added, and the reaction system was adjusted to pH 7.5 with 1 M Arg (Sigma-Aldrich, A5006-1KG) or 2 M Tris. The total weight was 0.5-2 mg.

2) The reaction system obtained in 1) was incubated at 37° C. for 5 h.

3) The buffer of the reaction system obtained in 2) was exchanged to PBS by centrifugation in an ultrafiltration/concentration tube. The mixture was naturally oxidized overnight at 4° C.

4) The two half molecules were assembled into molecules HDM010-012 in vitro by oxidation-reduction.

HIC-HPLC analysis of resultant molecules HDM010, 011 and 012: The solution obtained above was subjected to HIC-HPLC analysis on a high performance liquid chromatograph (Waters, model 2695) using MAbPac HIC-10 analytical column (Thermo, 088480) and the dimer obtained was purified in the following conditions: mobile phase A: 1.8 M $(NH_4)_2SO_4$, 100 mM $NaH_2PO_4$, pH 6.5; mobile phase B: 100 mM $NaH_2PO_4$:isopropanol=90:10 v/v, pH 6.5, flow rate: 1 mL/min; collecting time: 30 min; injection amount: 10 μL; column temperature: 25° C.; detection wavelength: 280 nm; injector temperature: 10° C. Elution gradient: 0-20 min, 100% A-100% B; 20-25 min, 100% B; 25-30 min, 100% A.

Figure 6:
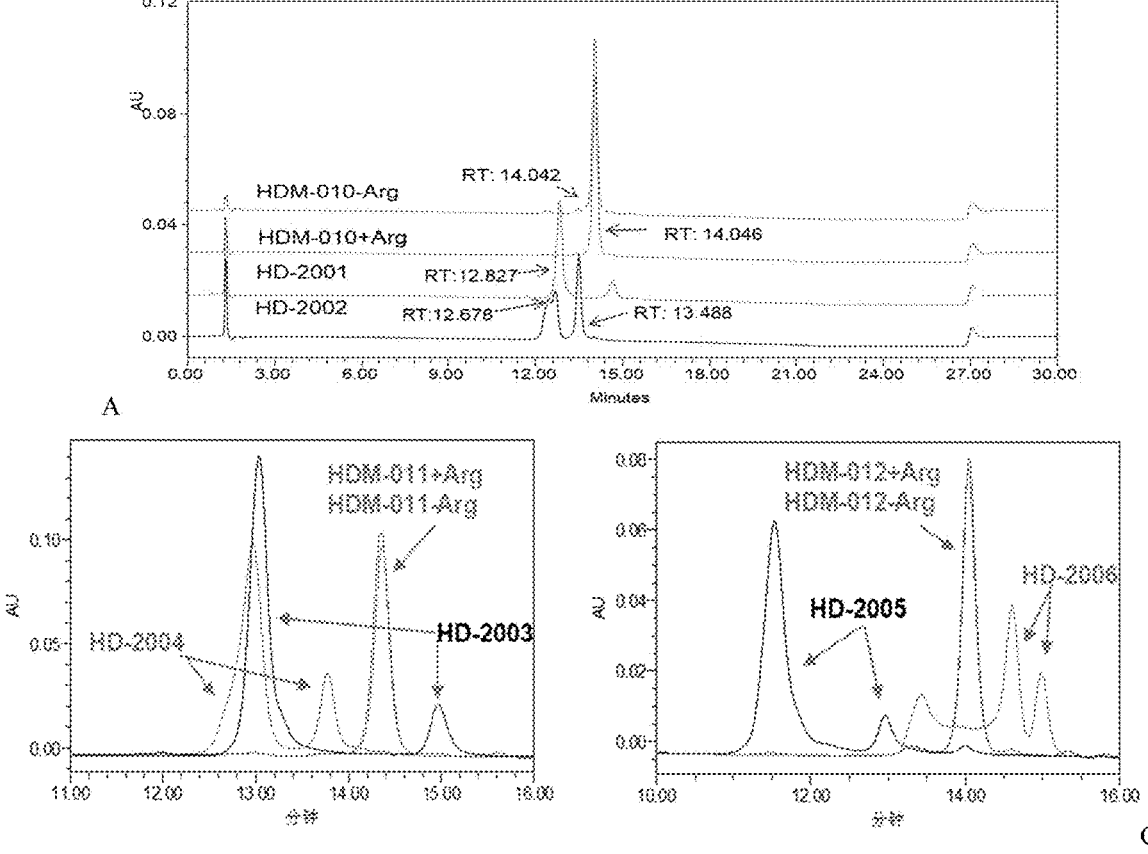
FIG. 6 shows the effect of L-arginine on Fc heterodimer assembly by HIC-HPLC.

The efficiency of Fc heterodimer assembly can be measured by HIC-HPLC. Since the half molecules differ in hydrophobicity from the assembled heterodimers, the time to peak in the HIC profile differs, thus distinguishing the assembled heterodimer molecules from the half molecules. As shown in FIG. 6A, the two half molecules HD-2001 and HD-2002 showed times to peak earlier than that of the assembled molecule HDM-010; as shown in FIG. 6B, the two half molecules HD-2003 and HD-2004 showed times to peak different from that of the assembled molecule HDM-011; as shown in FIG. 6C, the two half molecules HD-2005 and HD-2004 showed times to peak different from that of the assembled molecule HDM-012.

The assembly efficiency of Fc heterodimers with or without arginine addition was also assessed, as shown in Table 6.

TABLE 6

Effect of L-arginine on assembly efficiency of molecules

| Molecule | Half molecule combinations | Additive | Heterodimer proportion |
|---|---|---|---|
| HDM-010 – Arg | HD-2001 & HD-2002 | None | 92.20% |
| HDM-010 + Arg | HD-2001 & HD-2002 | L-arginine | 94.10% |
| HDM-011 – Arg | HD-2003 & HD-2004 | None | 89.35% |
| HDM-011 + Arg | HD-2003 & HD-2004 | L-arginine | 89.21% |
| HDM-012 – Arg | HD-2005 & HD-2006 | None | 89.15% |
| HDM-012 + Arg | HD-2005 & HD-2006 | L-arginine | 89.33% |

Example 5. Binding of Fc Heterodimers to Fc Receptors

The equilibrium dissociation constant (KD) for binding of the molecule HDM-006 of the present invention to human FcRn was determined by bio-layer interferometry (BLI). The BLI affinity assay was performed according to the existing methods (Estep, P et al., High throughput solution based measurement of antibody-antigen affinity and epitope binding. *MAbs,* 2013.5(2):p270-8).

Half an hour before the experiment, an appropriate number of HIS1K (Cat. No. 18-5020, Lot No. 2005073, Fortebio) sensors depending on the number of samples were soaked in SD buffer (1×PBS, BSA 0.1%, Tween-20 0.05%).

200 μL of SD buffer (1×PBS, BSA 0.1%, Tween-20 0.05%), HDM-006 of different concentrations, IgG1 (adalimumab) and human FcRn (Cat. No. CT009-H08H, Lot No. LC120C3101, Sino biological) were added to 96-well black polystyrene half-well microplates (Greiner, 655209). Detection was conducted using Fortebio Octet Red96, and the sensors were arranged according to the positions of the samples. After equilibration of sensors in SD buffer, 100 nM FcRn was immobilized before binding to antibodies of different concentrations (0, 25, 50 and 100 nM) and dissociation in SD buffer. The instrument settings were as follows: procedures: Baseline (60 s), Loading (100 s, ~1 nm), Baseline 1 (60 s), Association (60 s) and Dissociation (60 s), rotation speed: 1000 rpm, and temperature: 30° C. After the experiment was completed, KD values were analyzed using ForteBio Octet analysis software.

Figure 7:
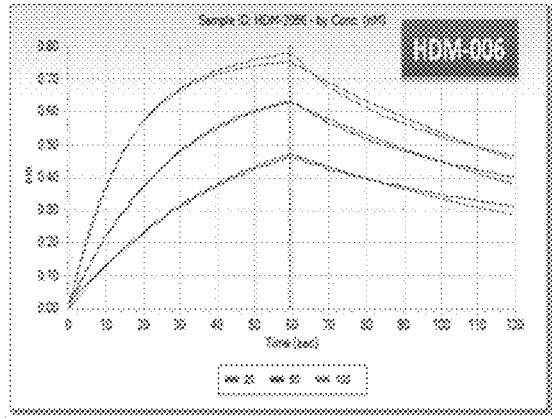
FIG. 7 shows the association/dissociation curves of an Fc heterodimer and an Fc wild-type antibody with FcRn.
Figure 7:
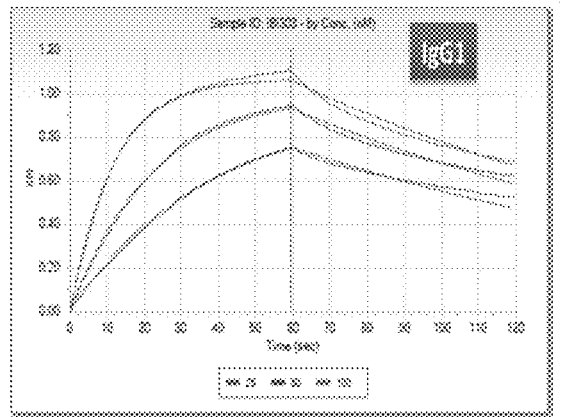

The experimental results are shown in FIG. 7 and Table 7. The affinity for FcRn was 9.88E-09 M for the control antibody IgG1 (adalimumab) and 1.43E-08 M for the Fc mutant (HDM-006) of the study, with a 1.4-fold difference that is within the detection error range of the instrument. Thus, the Fc heterodimers obtained in this study retain the binding capacity of the wild-type Fc to FcRn.

TABLE 7

Association/dissociation constant of Fc heterodimers and Fc wild-type antibodies to FcRn

| Sample ID | Antigen | KD (M) | kon(1/Ms) | kdis(1/s) |
|---|---|---|---|---|
| IgG1 | Human FcRn | 9.88E−09 | 7.80E+05 | 7.70E−03 |
| HDM-006 | | 1.43E−08 | 5.91E+05 | 8.42E−03 |

Example 6. Thermostability Evaluation of Fc Heterodimers

The thermostability of the antibodies can be detected by differential scanning fluorimetry (DSF). The protein undergoes structural changes with increasing temperature, thus exposing the hydrophobic region for binding to hydrophobic dyes. The fluorescence intensity of the dye changes with the amount of exposed hydrophobic aromatic amino acids, such that the change of the protein with the temperature can be determined according to the change of fluorescence intensity. The protein melting temperature Tm is the temperature corresponding to the maximum absolute value of the first derivative of fluorescence intensity change. Antibodies composed of multiple domains may exhibit multiple Tm values.

Monoclonal antibodies are proteins with good thermostability, and thermal denaturation analysis shows that the Tm (melting temperature) values of proteins are above 60° C., while the Tm of CH3 is >80° C. (Ionescu R M, *J Pharm. Sci.* 2008; 97:1414-26).

The molecules of this study were Fc heterodimers formed by interfacial amino acid mutations in CH3, and the influence of the mutations on the thermostability of the molecules was assessed by determination of the Tm of HDM-011 via DSF.

In the experiment, 5000× Sypro Orange dye (Cat No. 56650, Life Technologies) was diluted to 200× with ultrapure water, and then added to 1 mg/mL diluted samples (HDM-011) to adjust the dye concentration to 20× to give a mixture of the molecule and dye. The mixture was added to a PCR plate (Cat. No. 4306737, Applied Biosystems) at 30 μL per well and sealed with an optically transparent film (Cat. No. 4311971, Life Technologies). After centrifugation, the PCR plate was placed in ABI 7500 quantitative PCR system for detection. The initial temperature was 25° C., the equilibrium time was 5 min, the heating rate was 0.5%, the termination temperature was 99° C., and the holding time was 30 s. Tm values of samples were read after the experiment was completed. See FIG. 8 for the results.

Figure 8:
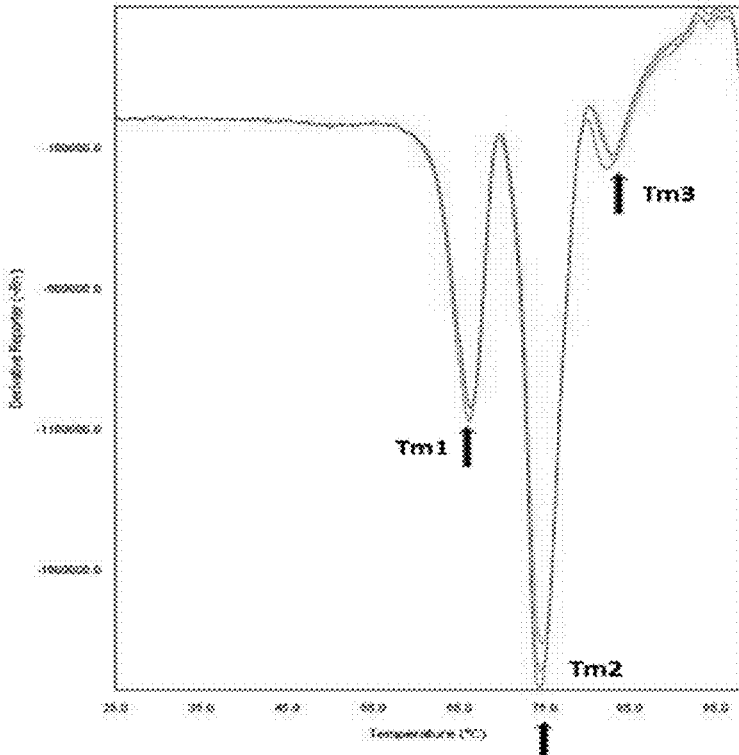
FIG. 8 shows the Tm of the Fc heterodimers by DSF.

As shown in FIG. 8, the Tm1, Tm2 and Tm3 of HDM-011 were 66.3° C., 74.6° C. and 83° C., respectively, suggesting that the CH3 mutations in this study will not reduce the thermostability of the molecule.

Sequence Listing

| SEQ ID NO | | Description and sequence |
|---|---|---|
| | Note | Anti-PD1 antibody (from WO2017024465A1) heavy chain HC |
| | CH3 mutation(s) | S364R, D399K, E357N, T350V |
| 1 | Full-length sequence | QVQLVQSGAEVKKPGSSVKVSCKASGGTFSSYAISWVRQA PGQGLEWMGLIIPMFDTAGYAQKFQGRVAITVDESTSTAY MELSSLRSEDTAVYYCARAEHSSTGTFDYWGQGTLVTVSS ASTKGPSVFPLAPSSKSTSGGTAALGCLVKDYFPEPVTVSW NSGALTSGVHTFPAVLQSSGLYSLSSVVTVPSSSLGTQTYIC |

| SEQ ID NO | Description and sequence |
|---|---|
| | Sequence Listing |
| | NVNHKPSNTKVDKKVEPKSCDKTHTCPPCPAPEAAGGPSV<br>FLFPPKPKDTLMISRTPEVTCVVVDVSHEDPEVKFNWYVD<br>GVEVHNAKTKPREEQYNSTYRVVSVLTVLHQDWLNGKEY<br>KCKVSNKALPAPIEKTISKAKGQPREPQVYVLPPSRDNLTK<br>NQVRLTCLVKGFYPSDIAVEWESNGQPENNYKTTPPVLKS<br>DGSFFLYSKLTVDKSRWQQGNVFSCSVMHEALHNHYTQK<br>SLSLSPGK |
| 21 | VH | QVQLVQSGAEVKKPGSSVKVSCKASGGTFSSYAISWVRQA<br>PGQGLEWMGLIIPMFDTAGYAQKFQGRVAITVDESTSTAY<br>MELSSLRSEDTAVYYCARAEHSSTGTFDYWGQGTLVTVSS |
| 22 | CH1 | ASTKGPSVFPLAPSSKSTSGGTAALGCLVKDYFPEPVTVSW<br>NSGALTSGVHTFPAVLQSSGLYSLSSVVTVPSSSLGTQTYIC<br>NVNHKPSNTKVDKKV |
| 23 | Hinge region | EPKSCDKTHTCPPCP |
| 24 | CH2 | APEAAGGPSVFLFPPKPKDTLMISRTPEVTCVVVDVSHEDP<br>EVKFNWYVDGVEVHNAKTKPREEQYNSTYRVVSVLTVLH<br>QDWLNGKEYKCKVSNKALPAPIEKTISKAK |
| 25 | CH3 | GQPREPQVYVLPPSRDNLTKNQVRLTCLVKGFYPSDIAVE<br>WESNGQPENNYKTTPPVLKSDGSFFLYSKLTVDKSRWQQG<br>NVFSCSVMHEALHNHYTQKSLSLSPGK |
| | Note | IL-2 mutant, by engineering in-house |
| | CH3 mutation(s) | K370S, Y349T, Q347D, K409D, T350V |
| 2 | Full-length sequence | APASSSTKKTQLQLEHLLLDLQMILNGINNYKNPELEEMLT<br>AKFYMPKKATELKHLQCLEEELKPLEEVLNLAGDASIHDLI<br>SNINVIVLELKGSETTFMCEYADETATIVEFLNRWITFSQSII<br>STLTGGGGSGGGGSDKTHTCPPCPAPEAAGGPSVFLFPPKP<br>KDTLMISRTPEVTCVVVDVSHEDPEVKFNWYVDGVEVHN<br>AKTKPREEQYNSTYRVVSVLTVLHQDWLNGKEYKCKVSN<br>KALPAPIEKTISKAKGQPREPDVTVLPPSRDELTKNQVSLTC<br>LVSGFYPSDIAVEWESNGQPENNYKTTPPVLDSDGSFFLYS<br>DLTVDKSRWQQGNVFSCSVMHEALHNHYTQKSLSLSPGK |
| 26 | IL-2 mutant protein | APASSSTKKTQLQLEHLLLDLQMILNGINNYKNPELEEMLT<br>AKFYMPKKATELKHLQCLEEELKPLEEVLNLAGDASIHDLI<br>SNINVIVLELKGSETTFMCEYADETATIVEFLNRWITFSQSII<br>STLT |
| 27 | Linker | GGGGSGGGGSDKTHTCPPCP |
| 24 | CH2 | APEAAGGPSVFLFPPKPKDTLMISRTPEVTCVVVDVSHEDP<br>EVKFNWYVDGVEVHNAKTKPREEQYNSTYRVVSVLTVLH<br>QDWLNGKEYKCKVSNKALPAPIEKTISKAK |
| 28 | CH3 | GQPREPDVTVLPPSRDELTKNQVSLTCLVSGFYPSDIAVEW<br>ESNGQPENNYKTTPPVLDSDGSFFLYSDLTVDKSRWQQGN<br>VFSCSVMHEALHNHYTQKSLSLSPGK |
| | Note | Anti-PD1 antibody (from WO2017024465A1) heavy chain HC |
| | CH3 mutation(s) | K409E, T411R |
| 3 | Full-length sequence | QVQLVQSGAEVKKPGSSVKVSCKASGGTFSSYAISWVRQA<br>PGQGLEWMGLIIPMFDTAGYAQKFQGRVAITVDESTSTAY<br>MELSSLRSEDTAVYYCARAEHSSTGTFDYWGQGTLVTVSS<br>ASTKGPSVFPLAPSSKSTSGGTAALGCLVKDYFPEPVTVSW<br>NSGALTSGVHTFPAVLQSSGLYSLSSVVTVPSSSLGTQTYIC<br>NVNHKPSNTKVDKKVEPKSCDKTHTCPPCPAPEAAGGPSV<br>FLFPPKPKDTLMISRTPEVTCVVVDVSHEDPEVKFNWYVD<br>GVEVHNAKTKPREEQYNSTYRVVSVLTVLHQDWLNGKEY<br>KCKVSNKALPAPIEKTISKAKGQPREPQVYTLPPSRDELTK<br>NQVSLTCLVKGFYPSDIAVEWESNGQPENNYKTTPPVLDS<br>DGSFFLYSELRVDKSRWQQGNVFSCSVMHEALHNHYTQK<br>SLSLSPGK |
| 21 | VH | QVQLVQSGAEVKKPGSSVKVSCKASGGTFSSYAISWVRQA<br>PGQGLEWMGLIIPMFDTAGYAQKFQGRVAITVDESTSTAY<br>MELSSLRSEDTAVYYCARAEHSSTGTFDYWGQGTLVTVSS |

| SEQ ID NO | Description and sequence | |
|---|---|---|

Sequence Listing

| SEQ ID NO | Description | sequence |
|---|---|---|
| 22 | CH1 | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKV |
| 23 | Hinge region | EPKSCDKTHTCPPCP |
| 24 | CH2 | APEAAGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAK |
| 29 | CH3 | GQPREPQVYTLPPSRDELTKNQVSLTCLVKGFYPSDIAVEW ESNGQPENNYKTTPPVLDSDGSFFLYSELRVDKSRWQQGN VFSCSVMHEALHNHYTQKSLSLSPGK |
| | Note | IL-2 mutant, by engineering in-house |
| | CH3 mutation(s) | D399K, K370T |
| 4 | Full-length sequence | APASSSTKKTQLQLEHLLLDLQMILNGINNYKNPELEEMLT AKFYMPKKATELKHLQCLEEELKPLEEVLNLAGDASIHDLI SNINVIVLELKGSETTFMCEYADETATIVEFLNRWITFSQSII STLTGGGGSGGGGSDKTHTCPPCPAPEAAGGPSVFLFPPKP KDTLMISRTPEVTCVVVDVSHEDPEVKFNWYVDGVEVHN AKTKPREEQYNSTYRVVSVLTVLHQDWLNGKEYKCKVSN KALPAPIEKTISKAKGQPREPQVYTLPPSRDELTKNQVSLTC LVTGFYPSDIAVEWESNGQPENNYKTTPPVLKSDGSFFLYS KLTVDKSRWQQGNVFSCSVMHEALHNHYTQKSLSLSPGK |
| 26 | IL-2 mutant protein | APASSSTKKTQLQLEHLLLDLQMILNGINNYKNPELEEMLT AKFYMPKKATELKHLQCLEEELKPLEEVLNLAGDASIHDLI SNINVIVLELKGSETTFMCEYADETATIVEFLNRWITFSQSII STLT |
| 27 | Linker | GGGGSGGGGSDKTHTCPPCP |
| 24 | CH2 | APEAAGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAK |
| 30 | CH3 | GQPREPQVYTLPPSRDELTKNQVSLTCLVTGFYPSDIAVEW ESNGQPENNYKTTPPVLKSDGSFFLYSKLTVDKSRWQQGN VFSCSVMHEALHNHYTQKSLSLSPGK |
| | Note | Anti-CD20 antibody (Rituxan) heavy chain HC |
| | CH3 mutation(s) | K370S, Y349T, Q347D, K409D, T350V |
| 5 | Full-length sequence | QVQLQQPGAELVKPGASVKMSCKASGYTFTSYNMHWVK QTPGRGLEWIGAIYPGNGDTSYNQKFKGKATLTADKSSSTA YMQLSSLTSEDSAVYYCARSTYYGGDWYFNVWGAGTTV TVSAASTKGPSVFPLAPSSKSTSGGTAALGCLVKDYFPEPV TVSWNSGALTSGVHTFPAVLQSSGLYSLSSVVTVPSSSLGT QTYICNVNHKPSNTKVDKKVEPKSCDKTHTCPPCPAPEAA GGPSVFLFPPKPKDTLMISRTPEVTCVVVDVSHEDPEVKFN WYVDGVEVHNAKTKPREEQYNSTYRVVSVLTVLHQDWL NGKEYKCKVSNKALPAPIEKTISKAKGQPREPDVTVLPPSR DELTKNQVSLTCLVSGFYPSDIAVEWESNGQPENNYKTTPP VLDSDGSFFLYSDLTVDKSRWQQGNVFSCSVMHEALHNH YTQKSLSLSPGK |
| 31 | VH | QVQLQQPGAELVKPGASVKMSCKASGYTFTSYNMHWVK QTPGRGLEWIGAIYPGNGDTSYNQKFKGKATLTADKSSSTA YMQLSSLTSEDSAVYYCARSTYYGGDWYFNVWGAGTTV TVSA |
| 22 | CH1 | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKV |
| 23 | Hinge region | EPKSCDKTHTCPPCP |
| 24 | CH2 | APEAAGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAK |

| Sequence Listing | | |
| --- | --- | --- |
| SEQ ID NO | Description and sequence | |

| 28 | CH3 | GQPREPDVTVLPPSRDELTKNQVSLTCLVSGFYPSDIAVEW ESNGQPENNYKTTPPVLDSDGSFFLYSDLTVDKSRWQQGN VFSCSVMHEALHNHYTQKSLSLSPGK |
| --- | --- | --- |
| | Note | Anti-PD1 antibody (from WO2017024465A1) heavy chain HC |
| | CH3 mutation(s) | S364R, D399K, E357N |
| 6 | Full-length sequence | QVQLVQSGAEVKKPGSSVKVSCKASGGTFSSYAISWVRQA PGQGLEWMGLIIPMFDTAGYAQKFQGRVAITVDESTSTAY MELSSLRSEDTAVYYCARAEHSSTGTFDYWGQGTLVTVSS ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPEAAGGPSV FLFPPKPKDTLMISRTPEVTCVVVDVSHEDPEVKFNWYVD GVEVHNAKTKPREEQYNSTYRVVSVLTVLHQDWLNGKEY KCKVSNKALPAPIEKTISKAKGQPREPQVYTLPPSRDNLTK NQVRLTCLVKGFYPSDIAVEWESNGQPENNYKTTPPVLKS DGSFFLYSKLTVDKSRWQQGNVFSCSVMHEALHNHYTQK SLSLSPGK |
| 21 | VH | QVQLVQSGAEVKKPGSSVKVSCKASGGTFSSYAISWVRQA PGQGLEWMGLIIPMFDTAGYAQKFQGRVAITVDESTSTAY MELSSLRSEDTAVYYCARAEHSSTGTFDYWGQGTLVTVSS |
| 22 | CH1 | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKV |
| 23 | Hinge region | EPKSCDKTHTCPPCP |
| 24 | CH2 | APEAAGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAK |
| 32 | CH3 | GQPREPQVYTLPPSRDNLTKNQVRLTCLVKGFYPSDIAVEW ESNGQPENNYKTTPPVLKSDGSFFLYSKLTVDKSRWQQGN VFSCSVMHEALHNHYTQKSLSLSPGK |
| | Note | Anti-PD1 antibody (from WO2017024465A1) heavy chain HC |
| | CH3 mutation(s) | S364R, D399K |
| 7 | Full-length sequence | QVQLVQSGAEVKKPGSSVKVSCKASGGTFSSYAISWVRQA PGQGLEWMGLIIPMFDTAGYAQKFQGRVAITVDESTSTAY MELSSLRSEDTAVYYCARAEHSSTGTFDYWGQGTLVTVSS ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPEAAGGPSV FLFPPKPKDTLMISRTPEVTCVVVDVSHEDPEVKFNWYVD GVEVHNAKTKPREEQYNSTYRVVSVLTVLHQDWLNGKEY KCKVSNKALPAPIEKTISKAKGQPREPQVYTLPPSRDELTK NQVRLTCLVKGFYPSDIAVEWESNGQPENNYKTTPPVLKS DGSFFLYSKLTVDKSRWQQGNVFSCSVMHEALHNHYTQK SLSLSPGK |
| 21 | VH | QVQLVQSGAEVKKPGSSVKVSCKASGGTFSSYAISWVRQA PGQGLEWMGLIIPMFDTAGYAQKFQGRVAITVDESTSTAY MELSSLRSEDTAVYYCARAEHSSTGTFDYWGQGTLVTVSS |
| 22 | CH1 | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKV |
| 23 | Hinge region | EPKSCDKTHTCPPCP |
| 24 | CH2 | APEAAGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAK |
| 33 | CH3 | GQPREPQVYTLPPSRDELTKNQVRLTCLVKGFYPSDIAVEW ESNGQPENNYKTTPPVLKSDGSFFLYSKLTVDKSRWQQGN VFSCSVMHEALHNHYTQKSLSLSPGK |

-continued

| Sequence Listing | | |
|---|---|---|
| SEQ ID NO | Description and sequence | |
| | Note | IL-2 mutant, by engineering in-house |
| | CH3 mutation(s) | K370S, Y349T, Q347D, K409D |
| 8 | Full-length sequence | APASSSTKKTQLQLEHLLLDLQMILNGINNYKNPELEEMLT<br>AKFYMPKKATELKHLQCLEEELKPLEEVLNLAGDASIHDLI<br>SNINVIVLELKGSETTFMCEYADETATIVEFLNRWITFSQSII<br>STLTGGGGSGGGGSDKTHTCPPCPAPEAAGGPSVFLFPPKP<br>KDTLMISRTPEVTCVVVDVSHEDPEVKFNWYVDGVEVHN<br>AKTKPREEQYNSTYRVVSVLTVLHQDWLNGKEYKCKVSN<br>KALPAPIEKTISKAKGQPREPDVTTLPPSRDELTKNQVSLTC<br>LVSGFYPSDIAVEWESNGQPENNYKTTPPVLDSDGSFFLYS<br>DLTVDKSRWQQGNVFSCSVMHEALHNHYTQKSLSLSPGK |
| 26 | IL-2 mutant protein | APASSSTKKTQLQLEHLLLDLQMILNGINNYKNPELEEMLT<br>AKFYMPKKATELKHLQCLEEELKPLEEVLNLAGDASIHDLI<br>SNINVIVLELKGSETTFMCEYADETATIVEFLNRWITFSQSII<br>STLT |
| 27 | Linker | GGGGSGGGGSDKTHTCPPCP |
| 24 | CH2 | APEAAGGPSVFLFPPKPKDTLMISRTPEVTCVVVDVSHEDP<br>EVKFNWYVDGVEVHNAKTKPREEQYNSTYRVVSVLTVLH<br>QDWLNGKEYKCKVSNKALPAPIEKTISKAK |
| 34 | CH3 | GQPREPDVTTLPPSRDELTKNQVSLTCLVSGFYPSDIAVEW<br>ESNGQPENNYKTTPPVLDSDGSFFLYSDLTVDKSRWQQGN<br>VFSCSVMHEALHNHYTQKSLSLSPGK |
| | Note | IL-2 mutant, by engineering in-house |
| | CH3 mutation(s) | K370S, Y349T, K409D |
| 9 | Full-length sequence | APASSSTKKTQLQLEHLLLDLQMILNGINNYKNPELEEMLT<br>AKFYMPKKATELKHLQCLEEELKPLEEVLNLAGDASIHDLI<br>SNINVIVLELKGSETTFMCEYADETATIVEFLNRWITFSQSII<br>STLTGGGGSGGGGSDKTHTCPPCPAPEAAGGPSVFLFPPKP<br>KDTLMISRTPEVTCVVVDVSHEDPEVKFNWYVDGVEVHN<br>AKTKPREEQYNSTYRVVSVLTVLHQDWLNGKEYKCKVSN<br>KALPAPIEKTISKAKGQPREPQVTTLPPSRDELTKNQVSLTC<br>LVSGFYPSDIAVEWESNGQPENNYKTTPPVLDSDGSFFLYS<br>DLTVDKSRWQQGNVFSCSVMHEALHNHYTQKSLSLSPGK |
| 26 | IL-2 mutant protein | APASSSTKKTQLQLEHLLLDLQMILNGINNYKNPELEEMLT<br>AKFYMPKKATELKHLQCLEEELKPLEEVLNLAGDASIHDLI<br>SNINVIVLELKGSETTFMCEYADETATIVEFLNRWITFSQSII<br>STLT |
| 27 | Linker | GGGGSGGGGSDKTHTCPPCP |
| 24 | CH2 | APEAAGGPSVFLFPPKPKDTLMISRTPEVTCVVVDVSHEDP<br>EVKFNWYVDGVEVHNAKTKPREEQYNSTYRVVSVLTVLH<br>QDWLNGKEYKCKVSNKALPAPIEKTISKAK |
| 35 | CH3 | GQPREPQVTTLPPSRDELTKNQVSLTCLVSGFYPSDIAVEW<br>ESNGQPENNYKTTPPVLDSDGSFFLYSDLTVDKSRWQQGN<br>VFSCSVMHEALHNHYTQKSLSLSPGK |
| | Note | Anti-CD20 antibody (Rituxan) heavy chain HC |
| | CH3 mutation(s) | S364R, D399K |
| 10 | Full-length sequence | QVQLQQPGAELVKPGASVKMSCKASGYTFTSYNMHWVK<br>QTPGRGLEWIGAIYPGNGDTSYNQKFKGKATLTADKSSSTA<br>YMQLSSLTSEDSAVYYCARSTYYGGDWYFNVWGAGTTV<br>TVSAASTKGPSVFPLAPSSKSTSGGTAALGCLVKDYFPEPV<br>TVSWNSGALTSGVHTFPAVLQSSGLYSLSSVVTVPSSSLGT<br>QTYICNVNHKPSNTKVDKKVEPKSCDKTHTCPPCPAPEAA<br>GGPSVFLFPPKPKDTLMISRTPEVTCVVVDVSHEDPEVKFN<br>WYVDGVEVHNAKTKPREEQYNSTYRVVSVLTVLHQDWL<br>NGKEYKCKVSNKALPAPIEKTISKAK<br>GQPREPQVYTLPPSRDELTKNQVRLTCLVKGFYPSDIAVEW<br>ESNGQPENNYKTTPPVLKSDGSFFLYSKLTVDKSRWQQGN<br>VFSCSVMHEALHNHYTQKSLSLSPGK |

| SEQ ID NO | Description and sequence | |
|---|---|---|

Sequence Listing

| SEQ ID NO | Description and sequence | |
|---|---|---|
| 31 | VH | QVQLQQPGAELVKPGASVKMSCKASGYTFTSYNMHWVK QTPGRGLEWIGAIYPGNGDTSYNQKFKGKATLTADKSSTA YMQLSSLTSEDSAVYYCARSTYYGGDWYFNVWGAGTTV TVSA |
| 22 | CH1 | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKV |
| 23 | Hinge region | EPKSCDKTHTCPPCP |
| 24 | CH2 | APEAAGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAK |
| 33 | CH3 | GQPREPQVYTLPPSRDELTKNQVRLTCLVKGFYPSDIAVEW ESNGQPENNYKTTPPVLKSDGSFFLYSKLTVDKSRWQQGN VFSCSVMHEALHNHYTQKSLSLSPGK |
| | Note | Anti-GPC3 antibody (from US7979086B2) heavy chain HC |
| | CH3 mutation(s) | S364R, D399K |
| 11 | Full-length sequence | QVQLVQSGAEVKKPGASVKVSCKASGYTFTDYEMHWVR QAPGQGLEWMGALDPKTGDTAYSQKFKGRVTLTADKSTS TAYMELSSLTSEDTAVYYCTRFYSYTYWGQGTLVTVSSAS TKGPSVFPLAPSSKSTSGGTAALGCLVKDYFPEPVTVSWNS GALTSGVHTFPAVLQSSGLYSLSSVVTVPSSSLGTQTYICNV NHKPSNTKVDKKVEPKSCDKTHTCPPCPAPEAAGGPSVFL FPPKPKDTLMISRTPEVTCVVVDVSHEDPEVKFNWYVDGV EVHNAKTKPREEQYNSTYRVVSVLTVLHQDWLNGKEYKC KVSNKALPAPIEKTISKAKGQPREPQVYTLPPSRDELTKNQ VRLTCLVKGFYPSDIAVEWESNGQPENNYKTTPPVLKSDG SFFLYSKLTVDKSRWQQGNVFSCSVMHEALHNHYTQKSLS LSPGK |
| 36 | VH | QVQLVQSGAEVKKPGASVKVSCKASGYTFTDYEMHWVR QAPGQGLEWMGALDPKTGDTAYSQKFKGRVTLTADKSTS TAYMELSSLTSEDTAVYYCTRFYSYTYWGQGTLVTVSS |
| 22 | CH1 | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKV |
| 23 | Hinge region | EPKSCDKTHTCPPCP |
| 24 | CH2 | APEAAGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAK |
| 33 | CH3 | GQPREPQVYTLPPSRDELTKNQVRLTCLVKGFYPSDIAVEW ESNGQPENNYKTTPPVLKSDGSFFLYSKLTVDKSRWQQGN VFSCSVMHEALHNHYTQKSLSLSPGK |
| | Note | Anti-PD1 antibody (from WO2017024465A1) heavy chain HC |
| | CH3 mutation(s) | K370S, Y349T, K409D |
| 12 | Full-length sequence | QVQLVQSGAEVKKPGSSVKVSCKASGGTFSSYAISWVRQA PGQGLEWMGLIIPMFDTAGYAQKFQGRVAITVDESTSTAY MELSSLRSEDTAVYYCARAEHSSTGTFDYWGQGTLVTVSS ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPEAAGGPSV FLFPPKPKDTLMISRTPEVTCVVVDVSHEDPEVKFNWYVD GVEVHNAKTKPREEQYNSTYRVVSVLTVLHQDWLNGKEY KCKVSNKALPAPIEKTISKAKGQPREPQVTTLPPSRDELTK NQVSLTCLVSGFYPSDIAVEWESNGQPENNYKTTPPVLDSD GSFFLYSDLTVDKSRWQQGNVFSCSVMHEALHNHYTQKS LSLSPGK |
| 21 | VH | QVQLVQSGAEVKKPGSSVKVSCKASGGTFSSYAISWVRQA PGQGLEWMGLIIPMFDTAGYAQKFQGRVAITVDESTSTAY MELSSLRSEDTAVYYCARAEHSSTGTFDYWGQGTLVTVSS |

-continued

| SEQ ID NO | Description and sequence | |
|---|---|---|
| | Sequence Listing | |
| 22 | CH1 | ASTKGPSVFPLAPSSKSTSGGTAALGCLVKDYFPEPVTVSW<br>NSGALTSGVHTFPAVLQSSGLYSLSSVVTVPSSSLGTQTYIC<br>NVNHKPSNTKVDKKV |
| 23 | Hinge region | EPKSCDKTHTCPPCP |
| 24 | CH2 | APEAAGGPSVFLFPPKPKDTLMISRTPEVTCVVVDVSHEDP<br>EVKFNWYVDGVEVHNAKTKPREEQYNSTYRVVSVLTVLH<br>QDWLNGKEYKCKVSNKALPAPIEKTISKAK |
| 35 | CH3 | GQPREPQVTTLPPSRDELTKNQVSLTCLVSGFYPSDIAVEW<br>ESNGQPENNYKTTPPVLDSDGSFFLYSDLTVDKSRWQQGN<br>VFSCSVMHEALHNHYTQKSLSLSPGK |
| | Note | Anti-PDL1 VHH (from CN109970860A) |
| | CH3 mutation(s) | K370S, Y349T, K409D |
| 13 | Full-length sequence | QVQLQESGGGLVQPGGSLRLSCAASAYTISRNSMGWFRQA<br>PGKGLEGVAAIESDGSTSYSDSVKGRFTISLDNSKNTLYLE<br>MNSLRAEDTAVYYCAAPKVGLGPRTALGHLAFMTLPALN<br>YWGQGTLVTVSSEPKSSDKTHTCPPCPAPEAAGGPSVFLFP<br>PKPKDTLMISRTPEVTCVVVDVSHEDPEVKFNWYVDGVE<br>VHNAKTKPREEQYNSTYRVVSVLTVLHQDWLNGKEYKC<br>KVSNKALPAPIEKTISKAKGQPREPQVTTLPPSRDELTKNQ<br>VSLTCLVSGFYPSDIAVEWESNGQPENNYKTTPPVLDSDGS<br>FFLYSDLTVDKSRWQQGNVFSCSVMHEALHNHYTQKSLS<br>LSPGK |
| 37 | VHH | QVQLQESGGGLVQPGGSLRLSCAASAYTISRNSMGWFRQA<br>PGKGLEGVAAIESDGSTSYSDSVKGRFTISLDNSKNTLYLE<br>MNSLRAEDTAVYYCAAPKVGLGPRTALGHLAFMTLPALN<br>YWGQGTLVTVSS |
| 38 | Hinge region | EPKSSDKTHTCPPCP |
| 24 | CH2 | APEAAGGPSVFLFPPKPKDTLMISRTPEVTCVVVDVSHEDP<br>EVKFNWYVDGVEVHNAKTKPREEQYNSTYRVVSVLTVLH<br>QDWLNGKEYKCKVSNKALPAPIEKTISKAK |
| 35 | CH3 | GQPREPQVTTLPPSRDELTKNQVSLTCLVSGFYPSDIAVEW<br>ESNGQPENNYKTTPPVLDSDGSFFLYSDLTVDKSRWQQGN<br>VFSCSVMHEALHNHYTQKSLSLSPGK |
| | Note | Anti-CD20 antibody (Rituxan) heavy chain HC |
| | CH3 mutation(s) | K370S, Y349T, K409D |
| 14 | Full-length sequence | QVQLQQPGAELVKPGASVKMSCKASGYTFTSYNMHWVK<br>QTPGRGLEWIGAIYPGNGDTSYNQKFKGKATLTADKSSSTA<br>YMQLSSLTSEDSAVYYCARSTYYGGDWYFNVWGAGTTV<br>TVSAASTKGPSVFPLAPSSKSTSGGTAALGCLVKDYFPEPV<br>TVSWNSGALTSGVHTFPAVLQSSGLYSLSSVVTVPSSSLGT<br>QTYICNVNHKPSNTKVDKKVEPKSCDKTHTCPPCPAPEAA<br>GGPSVFLFPPKPKDTLMISRTPEVTCVVVDVSHEDPEVKFN<br>WYVDGVEVHNAKTKPREEQYNSTYRVVSVLTVLHQDWL<br>NGKEYKCKVSNKALPAPIEKTISKAKGQPREPQVTTLPPSR<br>DELTKNQVSLTCLVSGFYPSDIAVEWESNGQPENNYKTTPP<br>VLDSDGSFFLYSDLTVDKSRWQQGNVFSCSVMHEALHNH<br>YTQKSLSLSPGK |
| 31 | VH | QVQLQQPGAELVKPGASVKMSCKASGYTFTSYNMHWVK<br>QTPGRGLEWIGAIYPGNGDTSYNQKFKGKATLTADKSSSTA<br>YMQLSSLTSEDSAVYYCARSTYYGGDWYFNVWGAGTTV<br>TVSA |
| 22 | CH1 | ASTKGPSVFPLAPSSKSTSGGTAALGCLVKDYFPEPVTVSW<br>NSGALTSGVHTFPAVLQSSGLYSLSSVVTVPSSSLGTQTYIC<br>NVNHKPSNTKVDKKV |
| 23 | Hinge region | EPKSCDKTHTCPPCP |
| 24 | CH2 | APEAAGGPSVFLFPPKPKDTLMISRTPEVTCVVVDVSHEDP<br>EVKFNWYVDGVEVHNAKTKPREEQYNSTYRVVSVLTVLH<br>QDWLNGKEYKCKVSNKALPAPIEKTISKAK |

-continued

| SEQ ID NO | Description and sequence |
|---|---|

Sequence Listing

| SEQ ID NO | | Description and sequence |
|---|---|---|
| 35 | CH3 | GQPREPQVTTLPPSRDELTKNQVSLTCLVSGFYPSDIAVEW ESNGQPENNYKTTPPVLDSDGSFFLYSDLTVDKSRWQQGN VFSCSVMHEALHNHYTQKSLSLSPGK |
| | Note | Anti-CD47 scFv (from CN109422811A) |
| | CH3 mutation(s) | K370S, Y349T, K409D |
| 15 | Full-length sequence | DIQMTQSPSSVSASVGDRVTITCRASQGISRWLAWYQQKP GKAPKLLIYAASSLQSGVPSRFSGSGSGTDFTLTISSLQPEDF ATYYCQQTVSFPITFGGGTKVEIKGGGGGGGGSGGGGSQ VQLQESGPGLVKPSETLSLTCTVSGGSIEHYYWSWIRQPPG KGLEWIGYIYYSGSTNYNPSLKSRVTISVDTSKNQFSLKLS SVTAADTAVYYCARGKTGSAAWGQGTLVTVSSDKTHTCP PCPAPEAAGGPSVFLFPPKPKDTLMISRTPEVTCVVVDVSH EDPEVKFNWYVDGVEVHNAKTKPREEQYNSTYRVVSVLT VLHQDWLNGKEYKCKVSNKALPAPIEKTISKAKGQPREPQ VTTLPPSRDELTKNQVSLTCLVSGFYPSDIAVEWESNGQPE NNYKTTPPVLDSDGSFFLYSDLTVDKSRWQQGNVFSCSVM HEALHNHYTQKSLSLSPGK |
| 39 | scFv | DIQMTQSPSSVSASVGDRVTITCRASQGISRWLAWYQQKP GKAPKLLIYAASSLQSGVPSRFSGSGSGTDFTLTISSLQPEDF ATYYCQQTVSFPITFGGGTKVEIKGGGGSGGGGSGGGGSQ VQLQESGPGLVKPSETLSLTCTVSGGSIEHYYWSWIRQPPG KGLEWIGYIYYSGSTNYNPSLKSRVTISVDTSKNQFSLKLS SVTAADTAVYYCARGKTGSAAWGQGTLVTVSS |
| 40 | Linker | DKTHTCPPCP |
| 24 | CH2 | APEAAGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAK |
| 35 | CH3 | GQPREPQVTTLPPSRDELTKNQVSLTCLVSGFYPSDIAVEW ESNGQPENNYKTTPPVLDSDGSFFLYSDLTVDKSRWQQGN VFSCSVMHEALHNHYTQKSLSLSPGK |
| | Note | Anti-HER2 antibody (pertuzumab) heavy chain HC |
| | CH3 mutation(s) | S364R, D399K |
| 16 | Full-length sequence | EVOLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVTV SSASTKGPSVFPLAPSSKSTSGGTAALGCLVKDYFPEPVTV SWNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLN GKEYKCKVSNKALPAPIEKTISKAKGQPREPQVYTLPPSRD ELTKNQVRLTCLVKGFYPSDIAVEWESNGQPENNYKTTPP VLKSDGSFFLYSKLTVDKSRWQQGNVFSCSVMHEALHNH YTQKSLSLSPGK |
| 41 | VH | EVOLVESGGGLVQPGGSLRLSCAASGFNIKDTYIHWVRQA PGKGLEWVARIYPTNGYTRYADSVKGRFTISADTSKNTAY LQMNSLRAEDTAVYYCSRWGGDGFYAMDYWGQGTLVTV SS |
| 22 | CH1 | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKV |
| 23 | Hinge region | EPKSCDKTHTCPPCP |
| 24 | CH2 | APEAAGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAK |
| 33 | CH3 | GQPREPQVYTLPPSRDELTKNQVRLTCLVKGFYPSDIAVEW ESNGQPENNYKTTPPVLKSDGSFFLYSKLTVDKSRWQQGN VFSCSVMHEALHNHYTQKSLSLSPGK |

-continued

| Sequence Listing | | |
|---|---|---|
| SEQ ID NO | Description and sequence | |

|  | Note | Anti-PD1 antibody (from WO2017024465A1) light chain LC |
|---|---|---|
|  | CH3 mutation(s) | N/A |
| 17 | Full-length sequence | DIQMTQSPSSVSASVGDRVTITCRASQGISSWLAWYQQKP<br>GKAPKLLISAASSLQSGVPSRFSGSGSGTDFTLTISSLQPEDF<br>ATYYCQQANHLPFTFGGGTKVEIKRTVAAPSVFIFPPSDEQ<br>LKSGTASVVCLLNNFYPREAKVQWKVDNALQSGNSQESV<br>TEQDSKDSTYSLSSTLTLSKADYEKHKVYACEVTHQGLSS<br>PVTKSFNRGEC |
| 42 | VL | DIQMTQSPSSVSASVGDRVTITCRASQGISSWLAWYQQKP<br>GKAPKLLISAASSLQSGVPSRFSGSGSGTDFTLTISSLQPEDF<br>ATYYCQQANHLPFTFGGGTKVEIK |
| 43 | CL | RTVAAPSVFIFPPSDEQLKSGTASVVCLLNNFYPREAKVQW<br>KVDNALQSGNSQESVTEQDSKDSTYSLSSTLTLSKADYEK<br>HKVYACEVTHQGLSSPVTKSFNRGEC |
|  | Note | Anti-HER2 antibody (pertuzumab) light chain LC |
|  | CH3 mutation(s) | N/A |
| 18 | Full-length sequence | DIQMTQSPSSLSASVGDRVTITCKASQDVSIGVAWYQQKPG<br>KAPKLLIYSASYRYTGVPSRFSGSGSGTDFTLTISSLQPEDFA<br>TYYCQQYYIYPYTFGQGTKVEIKRTVAAPSVFIFPPSDEQL<br>KSGTASVVCLLNNFYPREAKVQWKVDNALQSGNSQESVT<br>EQDSKDSTYSLSSTLTLSKADYEKHKVYACEVTHQGLSSP<br>VTKSFNRGEC |
| 44 | VL | DIQMTQSPSSLSASVGDRVTITCKASQDVSIGVAWYQQKPG<br>KAPKLLIYSASYRYTGVPSRFSGSGSGTDFTLTISSLQPEDFA<br>TYYCQQYYIYPYTFGQGTKVEIK |
| 43 | CL | RTVAAPSVFIFPPSDEQLKSGTASVVCLLNNFYPREAKVQW<br>KVDNALQSGNSQESVTEQDSKDSTYSLSSTLTLSKADYEK<br>HKVYACEVTHQGLSSPVTKSFNRGEC |
|  | Note | Anti-CD20 antibody (Rituxan) light chain LC |
|  | CH3 mutation(s) | N/A |
| 19 | Full-length sequence | QIVLSQSPAILSASPGEKVTMTCRASSSVSYIHWFQQKPGSS<br>PKPWIYATSNLASGVPVRFSGSGSGTSYSLTISRVEAEDAAT<br>YYCQQWTSNPPTFGGGTKLEIKRTVAAPSVFIFPPSDEQLK<br>SGTASVVCLLNNFYPREAKVQWKVDNALQSGNSQESVTE<br>QDSKDSTYSLSSTLTLSKADYEKHKVYACEVTHQGLSSPV<br>TKSFNRGEC |
| 45 | VL | QIVLSQSPAILSASPGEKVTMTCRASSSVSYIHWFQQKPGSS<br>PKPWIYATSNLASGVPVRFSGSGSGTSYSLTISRVEAEDAAT<br>YYCQQWTSNPPTFGGGTKLEIK |
| 43 | CL | RTVAAPSVFIFPPSDEQLKSGTASVVCLLNNFYPREAKVQW<br>KVDNALQSGNSQESVTEQDSKDSTYSLSSTLTLSKADYEK<br>HKVYACEVTHQGLSSPVTKSFNRGEC |
|  | Note | Anti-GPC3 antibody (from US7979086B2) light chain LC |
|  | CH3 mutation(s) | N/A |
| 20 | Full-length sequence | DVVMTQSPLSLPVTPGEPASISCRSSQSLVHSNRNTYLHWY<br>LQKPGQSPQLLIYKVSNRFSGVPDRFSGSGSGTDFTLKISRV<br>EAEDVGVYYCSQNTHVPPTFGQGTKLEIKRTVAAPSVFIFP<br>PSDEQLKSGTASVVCLLNNFYPREAKVQWKVDNALQSGN<br>SQESVTEQDSKDSTYSLSSTLTLSKADYEKHKVYACEVTH<br>QGLSSPVTKSFNRGEC |
| 46 | VL | DVVMTQSPLSLPVTPGEPASISCRSSQSLVHSNRNTYLHWY<br>LQKPGQSPQLLIYKVSNRFSGVPDRFSGSGSGTDFTLKISRV<br>EAEDVGVYYCSQNTHVPPTFGQGTKLEIK |

| Sequence Listing | | |
| --- | --- | --- |
| SEQ ID NO | | Description and sequence |
| 43 | CL | RTVAAPSVFIFPPSDEQLKSGTASVVCLLNNFYPREAKVQW<br>KVDNALQSGNSQESVTEQDSKDSTYSLSSTLTLSKADYEK<br>HKVYACEVTHQGLSSPVTKSFNRGEC<br>Wild-type IgG1, Uniprot: P01857 |
| 47 | CH | ASTKGPSVFPLAPSSKSTSGGTAALGCLVKDYFPEPVTVSW<br>NSGALTSGVHTFPAVLQSSGLYSLSSVVTVPSSSLGTQTYIC<br>NVNHKPSNTKVDKKVEPKSCDKTHTCPPCPAPELLGGPSV<br>FLFPPKPKDTLMISRTPEVTCVVVDVSHEDPEVKFNWYVD<br>GVEVHNAKTKPREEQYNSTYRVVSVLTVLHQDWLNGKEY<br>KCKVSNKALPAPIEKTISKAKGQPREPQVYTLPPSRDELTK<br>NQVSLTCLVKGFYPSDIAVEWESNGQPENNYKTTPPVLDS<br>DGSFFLYSKLTVDKSRWQQGNVFSCSVMHEALHNHYTQK<br>SLSLSPGK<br>Parent Fc (from IgG1) |
| 48 | CH2 + CH3 | DKTHTCPPCPAPELLGGPSVFLFPPKPKDTLMISRTPEVTCV<br>VVDVSHEDPEVKFNWYVDGVEVHNAKTKPREEQYNSTY<br>RVVSVLTVLHQDWLNGKEYKCKVSNKALPAPIEKTISKAK<br>GQPREPQVYTLPPSRDELTKNQVSLTCLVKGFYPSDIAVEW<br>ESNGQPENNYKTTPPVLDSDGSFFLYSKLTVDKSRWQQGN<br>VFSCSVMHEALHNHYTQKSLSLSPGK<br>Parent CH3 (Fc from IgG1) |
| 49 | CH3 | GQPREPQVYTLPPSRDELTKNQVSLTCLVKGFYPSDIAVEW<br>ESNGQPENNYKTTPPVLDSDGSFFLYSKLTVDKSRWQQGN<br>VFSCSVMHEALHNHYTQKSLSLSPGK |

The invention claimed is:

1. A heterodimeric Fc scaffold, comprising: a first Fc region comprising a first CH3 region, and a second Fc region comprising a second CH3 region, wherein the first CH3 region and the second CH3 region are different in sequence, wherein the heterodimeric interaction between the first CH3 region and the second CH3 region is stronger than the homodimeric interactions of the first CH3 region and the second CH3 region;

wherein, compared to a parent CH3 region, the first CH3 region comprises S364R and D399K, and the second CH3 region comprises K370S, Y349T and K409D, based on the EU numbering system; and wherein the parent CH3 region is a CH3 region from wild type human IgG1.

2. The heterodimeric Fc scaffold according to claim 1, wherein the first CH3 region further comprises E357N, and/or the second CH3 region further comprises Q347D.

3. The heterodimeric Fc scaffold according to claim 2, wherein either of the first CH3 region or the second CH3 region further comprises T350V, or both comprise T350V.

4. The heterodimeric Fc scaffold according to claim 1, wherein the first CH3 region and the second CH3 region have the following combinations of mutations:

(i) the first CH3 region comprises S364R, D399K, E357N and T350V, and the second CH3 region comprises K370S, Y349T, Q347D, K409D and T350V;

(ii) the first CH3 region comprises S364R, D399K and E357N, and the second CH3 region comprises K370S, Y349T, Q347D and K409D; or (iii) the first CH3 region comprises S364R and D399K, and the second CH3 region comprises K370S, Y349T, Q347D and K409D.

5. The heterodimeric Fc scaffold according to claim 1, wherein the first Fc region and the second Fc region further comprise a CH2 region; wherein the CH2 region comprises or consists of the amino acid sequence set forth in SEQ ID NO: 24.

6. The heterodimeric Fc scaffold according to claim 1, wherein the parent CH3 region comprises or consists of an amino acid sequence set forth in SEQ ID NO: 49.

7. An Fc heterodimer, comprising the heterodimeric Fc scaffold according to claim 1.

8. An Fc heterodimer, comprising: a first target-binding region comprising a first Fc region comprising a first CH3 region, and a second target-binding region comprising a second Fc region comprising a second CH3 region, wherein the first CH3 region and the second CH3 region are different in sequence, wherein the heterodimeric interaction between the first CH3 region and the second CH3 region is stronger than the homodimeric interactions of the first CH3 region and the second CH3 region; wherein the first CH3 region and the second CH3 region are as defined in claim 4.

9. The Fc heterodimer according to claim 8, wherein the target-binding region is an antigen-binding fragment linked to an Fc region, or wherein the target-binding region is a ligand.

10. The Fc heterodimer according to claim 8, wherein the first target-binding region and the second target-binding region bind to an antigen and a receptor, respectively.

11. The Fc heterodimer according to claim 8, wherein a) the first/second target-binding region comprises an Fab fragment derived from an antibody and the first/second Fc region linked thereto, the second/first target-binding region comprises a ligand and the second/first Fc region linked thereto;

b) the first/second target-binding region comprises an Fab fragment derived from an antibody and the first/second Fc region linked thereto, the second/first target-binding region comprises an scFv derived from an antibody and the second/first Fc region linked thereto;

c) the first/second target-binding region comprises an Fab fragment derived from an antibody and the first/second Fc region linked thereto, the second/first target-binding region comprises a VHH derived from an antibody and the second/first Fc region linked thereto;

d) the first/second target-binding region comprises an Fab fragment derived from an antibody and the first/second Fc region linked thereto, the second/first target-binding region comprises an Fab fragment derived from an antibody and the second/first Fc region linked thereto.

12. An Fc heterodimer, comprising the heterodimeric Fc scaffold according to claim 4.

13. The Fc heterodimer according to claim 8, wherein the target-binding region is Fab, VH region, VHH or scFv, linked to an Fc region, or wherein the target binding region is IL-2.

14. The Fc heterodimer according to claim 8, wherein the first target-binding region and the second target-binding region bind to an antigen and a receptor, respectively, wherein the antigen is selected from PD1, PDL1, PDL2, CD20, CD47, HER2 and GPC3, and wherein the receptor is IL-2R.

\* \* \* \* \*

SEQUENCE LISTING

<160> NUMBER OF SEQ ID NOS: 49

<210> SEQ ID NO 1
<211> LENGTH: 450
<212> TYPE: PRT
<213> ORGANISM: Artificial
<220> FEATURE:
<223> OTHER INFORMATION: Synthetic polypeptide

<400> SEQUENCE: 1

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Leu Ile Ile Pro Met Phe Asp Thr Ala Gly Tyr Ala Gln Lys Phe
    50                  55                  60

Gln Gly Arg Val Ala Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu His Ser Ser Thr Gly Thr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

-continued

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Val Leu Pro Pro Ser Arg Asp Asn Leu Thr Lys Asn Gln Val Arg Leu
                355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Lys Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly Lys
    450
```

```
<210> SEQ ID NO 2
<211> LENGTH: 366
<212> TYPE: PRT
<213> ORGANISM: Artificial
<220> FEATURE:
<223> OTHER INFORMATION: Synthetic polypeptide

<400> SEQUENCE: 2
```

```
Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Glu Leu Glu Glu Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60
```

-continued

```
Pro Leu Glu Glu Val Leu Asn Leu Ala Gly Asp Ala Ser Ile His Asp
65                  70                  75                  80

Leu Ile Ser Asn Ile Asn Val Ile Val Leu Glu Leu Lys Gly Ser Glu
                85                  90                  95

Thr Thr Phe Met Cys Glu Tyr Ala Asp Glu Thr Ala Thr Ile Val Glu
            100                 105                 110

Phe Leu Asn Arg Trp Ile Thr Phe Ser Gln Ser Ile Ile Ser Thr Leu
        115                 120                 125

Thr Gly Gly Gly Ser Gly Gly Gly Ser Asp Lys Thr His Thr
    130                 135                 140

Cys Pro Pro Cys Pro Ala Pro Glu Ala Ala Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Asp Val Thr Val Leu Pro Pro
            260                 265                 270

Ser Arg Asp Glu Leu Thr Lys Asn Gln Val Ser Leu Thr Cys Leu Val
            275                 280                 285

Ser Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Asp Leu Thr Val Asp Lys Ser Arg Trp
            325                 330                 335

Gln Gln Gly Asn Val Phe Ser Cys Ser Val Met His Glu Ala Leu His
        340                 345                 350

Asn His Tyr Thr Gln Lys Ser Leu Ser Leu Ser Pro Gly Lys
        355                 360                 365
```

```
<210> SEQ ID NO 3
<211> LENGTH: 450
<212> TYPE: PRT
<213> ORGANISM: Artificial
<220> FEATURE:
<223> OTHER INFORMATION: Synthetic polypeptide

<400> SEQUENCE: 3
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
        35                  40                  45

Gly Leu Ile Ile Pro Met Phe Asp Thr Ala Gly Tyr Ala Gln Lys Phe
    50                  55                  60
```

```
Gln Gly Arg Val Ala Ile Thr Val Asp Glu Ser Thr Ser Thr Ala Tyr
65              70                  75                  80

Met Glu Leu Ser Ser Leu Arg Ser Glu Asp Thr Ala Val Tyr Tyr Cys
                85                  90                  95

Ala Arg Ala Glu His Ser Ser Thr Gly Thr Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Glu Leu Arg Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 4
<211> LENGTH: 366
```

<212> TYPE: PRT
<213> ORGANISM: Artificial
<220> FEATURE:
<223> OTHER INFORMATION: Synthetic polypeptide

<400> SEQUENCE: 4

```
Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Glu Leu Glu Glu Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gly Asp Ala Ser Ile His Asp
65                  70                  75                  80

Leu Ile Ser Asn Ile Asn Val Ile Val Leu Glu Leu Lys Gly Ser Glu
                85                  90                  95

Thr Thr Phe Met Cys Glu Tyr Ala Asp Glu Thr Ala Thr Ile Val Glu
                100                 105                 110

Phe Leu Asn Arg Trp Ile Thr Phe Ser Gln Ser Ile Ile Ser Thr Leu
        115                 120                 125

Thr Gly Gly Gly Gly Ser Gly Gly Gly Gly Ser Asp Lys Thr His Thr
    130                 135                 140

Cys Pro Pro Cys Pro Ala Pro Glu Ala Ala Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
                180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
                260                 265                 270

Ser Arg Asp Glu Leu Thr Lys Asn Gln Val Ser Leu Thr Cys Leu Val
        275                 280                 285

Thr Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Lys Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
        340                 345                 350

Asn His Tyr Thr Gln Lys Ser Leu Ser Leu Ser Pro Gly Lys
        355                 360                 365
```

<210> SEQ ID NO 5
<211> LENGTH: 451

-continued

<212> TYPE: PRT
<213> ORGANISM: Artificial
<220> FEATURE:
<223> OTHER INFORMATION: Synthetic polypeptide

<400> SEQUENCE: 5

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Asp Val
            340                 345                 350

Thr Val Leu Pro Pro Ser Arg Asp Glu Leu Thr Lys Asn Gln Val Ser
        355                 360                 365

Leu Thr Cys Leu Val Ser Gly Phe Tyr Pro Ser Asp Ile Ala Val Glu
        370                 375                 380
```

```
Trp Glu Ser Asn Gly Gln Pro Glu Asn Asn Tyr Lys Thr Thr Pro Pro
385             390             395             400

Val Leu Asp Ser Asp Gly Ser Phe Phe Leu Tyr Ser Asp Leu Thr Val
                405             410             415

Asp Lys Ser Arg Trp Gln Gln Gly Asn Val Phe Ser Cys Ser Val Met
                420             425             430

His Glu Ala Leu His Asn His Tyr Thr Gln Lys Ser Leu Ser Leu Ser
            435             440             445

Pro Gly Lys
    450

<210> SEQ ID NO 6
<211> LENGTH: 450
<212> TYPE: PRT
<213> ORGANISM: Artificial
<220> FEATURE:
<223> OTHER INFORMATION: Synthetic polypeptide

<400> SEQUENCE: 6

Gln Val Gln Leu Val Gln Ser Gly Ala Glu Val Lys Lys Pro Gly Ser
1               5               10              15

Ser Val Lys Val Ser Cys Lys Ala Ser Gly Gly Thr Phe Ser Ser Tyr
                20              25              30

Ala Ile Ser Trp Val Arg Gln Ala Pro Gly Gln Gly Leu Glu Trp Met
            35              40              45

Gly Leu Ile Ile Pro Met Phe Asp Thr Ala Gly Tyr Ala Gln Lys Phe
        50              55              60

Gln Gly Arg Val Ala Ile Thr Val Asp Glu Ser Thr Ser Thr Ala Tyr
65              70              75              80

Met Glu Leu Ser Ser Leu Arg Ser Glu Asp Thr Ala Val Tyr Tyr Cys
                85              90              95

Ala Arg Ala Glu His Ser Ser Thr Gly Thr Phe Asp Tyr Trp Gly Gln
            100             105             110

Gly Thr Leu Val Thr Val Ser Ser Ala Ser Thr Lys Gly Pro Ser Val
            115             120             125

Phe Pro Leu Ala Pro Ser Ser Lys Ser Thr Ser Gly Gly Thr Ala Ala
        130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
            180             185             190

Ser Ser Ser Leu Gly Thr Gln Thr Tyr Ile Cys Asn Val Asn His Lys
            195             200             205

Pro Ser Asn Thr Lys Val Asp Lys Lys Val Glu Pro Lys Ser Cys Asp
        210             215             220

Lys Thr His Thr Cys Pro Pro Cys Pro Ala Pro Glu Ala Ala Gly Gly
225             230             235             240

Pro Ser Val Phe Leu Phe Pro Pro Lys Pro Lys Asp Thr Leu Met Ile
            245             250             255

Ser Arg Thr Pro Glu Val Thr Cys Val Val Val Asp Val Ser His Glu
            260             265             270

Asp Pro Glu Val Lys Phe Asn Trp Tyr Val Asp Gly Val Glu Val His
        275             280             285
```

-continued

```
Asn Ala Lys Thr Lys Pro Arg Glu Glu Gln Tyr Asn Ser Thr Tyr Arg
    290             295                 300
```

```
Val Val Ser Val Leu Thr Val Leu His Gln Asp Trp Leu Asn Gly Lys
305             310                 315                 320
```

```
Glu Tyr Lys Cys Lys Val Ser Asn Lys Ala Leu Pro Ala Pro Ile Glu
            325                 330                 335
```

```
Lys Thr Ile Ser Lys Ala Lys Gly Gln Pro Arg Glu Pro Gln Val Tyr
            340                 345                 350
```

```
Thr Leu Pro Pro Ser Arg Asp Asn Leu Thr Lys Asn Gln Val Arg Leu
        355                 360                 365
```

```
Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400
```

```
Leu Lys Ser Asp Gly Ser Phe Phe Leu Tyr Ser Lys Leu Thr Val Asp
            405                 410                 415
```

```
Lys Ser Arg Trp Gln Gln Gly Asn Val Phe Ser Cys Ser Val Met His
            420                 425                 430
```

```
Glu Ala Leu His Asn His Tyr Thr Gln Lys Ser Leu Ser Leu Ser Pro
        435                 440                 445
```

```
Gly Lys
    450
```

```
<210> SEQ ID NO 7
<211> LENGTH: 450
<212> TYPE: PRT
<213> ORGANISM: Artificial
<220> FEATURE:
<223> OTHER INFORMATION: Synthetic polypeptide
```

```
<400> SEQUENCE: 7
```

```
Gln Val Gln Leu Val Gln Ser Gly Ala Glu Val Lys Lys Pro Gly Ser
1               5                   10                  15
```

```
Ser Val Lys Val Ser Cys Lys Ala Ser Gly Gly Thr Phe Ser Ser Tyr
            20                  25                  30
```

```
Ala Ile Ser Trp Val Arg Gln Ala Pro Gly Gln Gly Leu Glu Trp Met
        35                  40                  45
```

```
Gly Leu Ile Ile Pro Met Phe Asp Thr Ala Gly Tyr Ala Gln Lys Phe
    50                  55                  60
```

```
Gln Gly Arg Val Ala Ile Thr Val Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
            85                  90                  95
```

```
Ala Arg Ala Glu His Ser Ser Thr Gly Thr Phe Asp Tyr Trp Gly Gln
            100                 105                 110
```

```
Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
    130                 135                 140
```

```
Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
            165                 170                 175
```

```
Leu Gln Ser Ser Gly Leu Tyr Ser Leu Ser Ser Val Val Thr Val Pro
            180                 185                 190
```

-continued

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Arg Leu
                355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Lys Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly Lys
    450

<210> SEQ ID NO 8
<211> LENGTH: 366
<212> TYPE: PRT
<213> ORGANISM: Artificial
<220> FEATURE:
<223> OTHER INFORMATION: Synthetic polypeptide

<400> SEQUENCE: 8

Ala Pro Ala Ser Ser Ser Thr Lys Lys Thr Gln Leu Gln Leu Glu His
1                   5                   10                  15

Leu Leu Leu Asp Leu Gln Met Ile Leu Asn Gly Ile Asn Asn Tyr Lys
                20                  25                  30

Asn Pro Glu Leu Glu Glu Met Leu Thr Ala Lys Phe Tyr Met Pro Lys
                35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gly Asp Ala Ser Ile His Asp
65                  70                  75                  80

Leu Ile Ser Asn Ile Asn Val Ile Val Leu Glu Leu Lys Gly Ser Glu
                85                  90                  95

-continued

```
Thr Thr Phe Met Cys Glu Tyr Ala Asp Glu Thr Ala Thr Ile Val Glu
            100                 105                 110

Phe Leu Asn Arg Trp Ile Thr Phe Ser Gln Ser Ile Ile Ser Thr Leu
            115                 120                 125

Thr Gly Gly Gly Ser Gly Gly Gly Gly Ser Asp Lys Thr His Thr
    130                 135                 140

Cys Pro Pro Cys Pro Ala Pro Glu Ala Ala Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
            195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Asp Val Thr Thr Leu Pro Pro
            260                 265                 270

Ser Arg Asp Glu Leu Thr Lys Asn Gln Val Ser Leu Thr Cys Leu Val
            275                 280                 285

Ser Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Asp Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
            355                 360                 365

<210> SEQ ID NO 9
<211> LENGTH: 366
<212> TYPE: PRT
<213> ORGANISM: Artificial
<220> FEATURE:
<223> OTHER INFORMATION: Synthetic polypeptide

<400> SEQUENCE: 9

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Glu Leu Glu Glu Met Leu Thr Ala Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gly Asp Ala Ser Ile His Asp
65                  70                  75                  80

Leu Ile Ser Asn Ile Asn Val Ile Val Leu Glu Leu Lys Gly Ser Glu
                85                  90                  95
```

-continued

```
Thr Thr Phe Met Cys Glu Tyr Ala Asp Glu Thr Ala Thr Ile Val Glu
            100                 105                 110

Phe Leu Asn Arg Trp Ile Thr Phe Ser Gln Ser Ile Ile Ser Thr Leu
            115                 120                 125

Thr Gly Gly Gly Gly Ser Gly Gly Gly Gly Ser Asp Lys Thr His Thr
            130                 135                 140

Cys Pro Pro Cys Pro Ala Pro Glu Ala Ala Gly Gly Pro Ser Val Phe
145                 150                 155                 160

Leu Phe Pro Pro Lys Pro Lys Asp Thr Leu Met Ile Ser Arg Thr Pro
                    165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
            195                 200                 205

Lys Pro Arg Glu Glu Gln Tyr Asn Ser Thr Tyr Arg Val Val Ser Val
            210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                    245                 250                 255

Lys Ala Lys Gly Gln Pro Arg Glu Pro Gln Val Thr Thr Leu Pro Pro
            260                 265                 270

Ser Arg Asp Glu Leu Thr Lys Asn Gln Val Ser Leu Thr Cys Leu Val
            275                 280                 285

Ser Gly Phe Tyr Pro Ser Asp Ile Ala Val Glu Trp Glu Ser Asn Gly
            290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Asp Leu Thr Val Asp Lys Ser Arg Trp
                    325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
            355                 360                 365
```

```
<210> SEQ ID NO 10
<211> LENGTH: 451
<212> TYPE: PRT
<213> ORGANISM: Artificial
<220> FEATURE:
<223> OTHER INFORMATION: Synthetic polypeptide

<400> SEQUENCE: 10
```

```
Gln Val Gln Leu Gln Gln Pro Gly Ala Glu Leu Val Lys Pro Gly Ala
1                   5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
            50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                    85                  90                  95
```

-continued

```
Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
            210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Arg
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Lys Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450
```

```
<210> SEQ ID NO 11
<211> LENGTH: 445
<212> TYPE: PRT
<213> ORGANISM: Artificial
<220> FEATURE:
<223> OTHER INFORMATION: Synthetic polypeptide

<400> SEQUENCE: 11
```

-continued

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Arg Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Lys Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
```

-continued

```
                420               425               430

His Tyr Thr Gln Lys Ser Leu Ser Leu Ser Pro Gly Lys
        435               440               445

<210> SEQ ID NO 12
<211> LENGTH: 450
<212> TYPE: PRT
<213> ORGANISM: Artificial
<220> FEATURE:
<223> OTHER INFORMATION: Synthetic polypeptide

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Leu Ile Ile Pro Met Phe Asp Thr Ala Gly Tyr Ala Gln Lys Phe
    50                  55                  60

Gln Gly Arg Val Ala Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu His Ser Ser Thr Gly Thr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Thr
```

-continued

```
                 340                 345                 350
Thr Leu Pro Pro Ser Arg Asp Glu Leu Thr Lys Asn Gln Val Ser Leu
            355                 360                 365

Thr Cys Leu Val Ser Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Asp Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 13
<211> LENGTH: 364
<212> TYPE: PRT
<213> ORGANISM: Artificial
<220> FEATURE:
<223> OTHER INFORMATION: Synthetic polypeptide

<400> SEQUENCE: 13

```
Gln Val Gln Leu Gln Glu Ser Gly Gly Gly Leu Val Gln Pro Gly Gly
1               5                   10                  15

Ser Leu Arg Leu Ser Cys Ala Ala Ser Ala Tyr Thr Ile Ser Arg Asn
            20                  25                  30

Ser Met Gly Trp Phe Arg Gln Ala Pro Gly Lys Gly Leu Glu Gly Val
        35                  40                  45

Ala Ala Ile Glu Ser Asp Gly Ser Thr Ser Tyr Ser Asp Ser Val Lys
    50                  55                  60

Gly Arg Phe Thr Ile Ser Leu Asp Asn Ser Lys Asn Thr Leu Tyr Leu
65                  70                  75                  80

Glu Met Asn Ser Leu Arg Ala Glu Asp Thr Ala Val Tyr Tyr Cys Ala
                85                  90                  95

Ala Pro Lys Val Gly Leu Gly Pro Arg Thr Ala Leu Gly His Leu Ala
            100                 105                 110

Phe Met Thr Leu Pro Ala Leu Asn Tyr Trp Gly Gln Gly Thr Leu Val
        115                 120                 125

Thr Val Ser Ser Glu Pro Lys Ser Ser Asp Lys Thr His Thr Cys Pro
    130                 135                 140

Pro Cys Pro Ala Pro Glu Ala Ala Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
```

-continued

```
                245             250             255

Lys Gly Gln Pro Arg Glu Pro Gln Val Thr Thr Leu Pro Pro Ser Arg
            260             265             270

Asp Glu Leu Thr Lys Asn Gln Val Ser Leu Thr Cys Leu Val Ser Gly
        275             280             285

Phe Tyr Pro Ser Asp Ile Ala Val Glu Trp Glu Ser Asn Gly Gln Pro
    290             295             300

Glu Asn Asn Tyr Lys Thr Thr Pro Pro Val Leu Asp Ser Asp Gly Ser
305             310             315             320

Phe Phe Leu Tyr Ser Asp Leu Thr Val Asp Lys Ser Arg Trp Gln Gln
            325             330             335

Gly Asn Val Phe Ser Cys Ser Val Met His Glu Ala Leu His Asn His
            340             345             350

Tyr Thr Gln Lys Ser Leu Ser Leu Ser Pro Gly Lys
            355             360

<210> SEQ ID NO 14
<211> LENGTH: 451
<212> TYPE: PRT
<213> ORGANISM: Artificial
<220> FEATURE:
<223> OTHER INFORMATION: Synthetic polypeptide

<400> SEQUENCE: 14

Gln Val Gln Leu Gln Gln Pro Gly Ala Glu Leu Val Lys Pro Gly Ala
1               5               10              15

Ser Val Lys Met Ser Cys Lys Ala Ser Gly Tyr Thr Phe Thr Ser Tyr
            20              25              30

Asn Met His Trp Val Lys Gln Thr Pro Gly Arg Gly Leu Glu Trp Ile
        35              40              45

Gly Ala Ile Tyr Pro Gly Asn Gly Asp Thr Ser Tyr Asn Gln Lys Phe
    50              55              60

Lys Gly Lys Ala Thr Leu Thr Ala Asp Lys Ser Ser Ser Thr Ala Tyr
65              70              75              80

Met Gln Leu Ser Ser Leu Thr Ser Glu Asp Ser Ala Val Tyr Tyr Cys
            85              90              95

Ala Arg Ser Thr Tyr Tyr Gly Gly Asp Trp Tyr Phe Asn Val Trp Gly
            100             105             110

Ala Gly Thr Thr Val Thr Val Ser Ala Ala Ser Thr Lys Gly Pro Ser
            115             120             125

Val Phe Pro Leu Ala Pro Ser Ser Lys Ser Thr Ser Gly Gly Thr Ala
    130             135             140

Ala Leu Gly Cys Leu Val Lys Asp Tyr Phe Pro Glu Pro Val Thr Val
145             150             155             160

Ser Trp Asn Ser Gly Ala Leu Thr Ser Gly Val His Thr Phe Pro Ala
            165             170             175

Val Leu Gln Ser Ser Gly Leu Tyr Ser Leu Ser Ser Val Val Thr Val
            180             185             190

Pro Ser Ser Ser Leu Gly Thr Gln Thr Tyr Ile Cys Asn Val Asn His
            195             200             205

Lys Pro Ser Asn Thr Lys Val Asp Lys Lys Val Glu Pro Lys Ser Cys
    210             215             220

Asp Lys Thr His Thr Cys Pro Pro Cys Pro Ala Pro Glu Ala Ala Gly
225             230             235             240

Gly Pro Ser Val Phe Leu Phe Pro Pro Lys Pro Lys Asp Thr Leu Met
```

-continued

```
                    245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Thr Thr Leu Pro Pro Ser Arg Asp Glu Leu Thr Lys Asn Gln Val Ser
            355                 360                 365

Leu Thr Cys Leu Val Ser Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Asp Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 15
<211> LENGTH: 464
<212> TYPE: PRT
<213> ORGANISM: Artificial
<220> FEATURE:
<223> OTHER INFORMATION: Synthetic polypeptide

<400> SEQUENCE: 15

Asp Ile Gln Met Thr Gln Ser Pro Ser Ser Val Ser Ala Ser Val Gly
1                   5                   10                  15

Asp Arg Val Thr Ile Thr Cys Arg Ala Ser Gln Gly Ile Ser Arg Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Val Ser Phe Pro Ile
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gln Val Gln Leu Gln Glu
            115                 120                 125

Ser Gly Pro Gly Leu Val Lys Pro Ser Glu Thr Leu Ser Leu Thr Cys
        130                 135                 140

Thr Val Ser Gly Gly Ser Ile Glu His Tyr Tyr Trp Ser Trp Ile Arg
```

-continued

```
145                150                155                160
Gln Pro Pro Gly Lys Gly Leu Glu Trp Ile Gly Tyr Ile Tyr Tyr Ser
                165                170                175

Gly Ser Thr Asn Tyr Asn Pro Ser Leu Lys Ser Arg Val Thr Ile Ser
                180                185                190

Val Asp Thr Ser Lys Asn Gln Phe Ser Leu Lys Leu Ser Ser Val Thr
                195                200                205

Ala Ala Asp Thr Ala Val Tyr Tyr Cys Ala Arg Gly Lys Thr Gly Ser
    210                215                220

Ala Ala Trp Gly Gln Gly Thr Leu Val Thr Val Ser Ser Asp Lys Thr
225                230                235                240

His Thr Cys Pro Pro Cys Pro Ala Pro Glu Ala Ala Gly Gly Pro Ser
                245                250                255

Val Phe Leu Phe Pro Pro Lys Pro Lys Asp Thr Leu Met Ile Ser Arg
                260                265                270

Thr Pro Glu Val Thr Cys Val Val Val Asp Val Ser His Glu Asp Pro
                275                280                285

Glu Val Lys Phe Asn Trp Tyr Val Asp Gly Val Glu Val His Asn Ala
    290                295                300

Lys Thr Lys Pro Arg Glu Glu Gln Tyr Asn Ser Thr Tyr Arg Val Val
305                310                315                320

Ser Val Leu Thr Val Leu His Gln Asp Trp Leu Asn Gly Lys Glu Tyr
                325                330                335

Lys Cys Lys Val Ser Asn Lys Ala Leu Pro Ala Pro Ile Glu Lys Thr
                340                345                350

Ile Ser Lys Ala Lys Gly Gln Pro Arg Glu Pro Gln Val Thr Thr Leu
                355                360                365

Pro Pro Ser Arg Asp Glu Leu Thr Lys Asn Gln Val Ser Leu Thr Cys
    370                375                380

Leu Val Ser Gly Phe Tyr Pro Ser Asp Ile Ala Val Glu Trp Glu Ser
385                390                395                400

Asn Gly Gln Pro Glu Asn Asn Tyr Lys Thr Thr Pro Pro Val Leu Asp
                405                410                415

Ser Asp Gly Ser Phe Phe Leu Tyr Ser Asp Leu Thr Val Asp Lys Ser
                420                425                430

Arg Trp Gln Gln Gly Asn Val Phe Ser Cys Ser Val Met His Glu Ala
                435                440                445

Leu His Asn His Tyr Thr Gln Lys Ser Leu Ser Leu Ser Pro Gly Lys
    450                455                460
```

```
<210> SEQ ID NO 16
<211> LENGTH: 450
<212> TYPE: PRT
<213> ORGANISM: Artificial
<220> FEATURE:
<223> OTHER INFORMATION: Synthetic polypeptide

<400> SEQUENCE: 16

Glu Val Gln Leu Val Glu Ser Gly Gly Gly Leu Val Gln Pro Gly Gly
1                5                10                15

Ser Leu Arg Leu Ser Cys Ala Ala Ser Gly Phe Asn Ile Lys Asp Thr
                20                25                30

Tyr Ile His Trp Val Arg Gln Ala Pro Gly Lys Gly Leu Glu Trp Val
                35                40                45

Ala Arg Ile Tyr Pro Thr Asn Gly Tyr Thr Arg Tyr Ala Asp Ser Val
```

-continued

```
              50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Arg Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Lys Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450
```

<210> SEQ ID NO 17

```
<211> LENGTH: 214
<212> TYPE: PRT
<213> ORGANISM: Artificial
<220> FEATURE:
<223> OTHER INFORMATION: Synthetic polypeptide

<400> SEQUENCE: 17

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn His Leu Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 18
<211> LENGTH: 214
<212> TYPE: PRT
<213> ORGANISM: Artificial
<220> FEATURE:
<223> OTHER INFORMATION: Synthetic polypeptide

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
```

-continued

```
                 100              105              110

Pro Ser Val Phe Ile Phe Pro Pro Ser Asp Glu Gln Leu Lys Ser Gly
        115              120              125

Thr Ala Ser Val Val Cys Leu Leu Asn Asn Phe Tyr Pro Arg Glu Ala
    130              135              140

Lys Val Gln Trp Lys Val Asp Asn Ala Leu Gln Ser Gly Asn Ser Gln
145              150              155              160

Glu Ser Val Thr Glu Gln Asp Ser Lys Asp Ser Thr Tyr Ser Leu Ser
             165              170              175

Ser Thr Leu Thr Leu Ser Lys Ala Asp Tyr Glu Lys His Lys Val Tyr
             180              185              190

Ala Cys Glu Val Thr His Gln Gly Leu Ser Ser Pro Val Thr Lys Ser
        195              200              205

Phe Asn Arg Gly Glu Cys
    210
```

```
<210> SEQ ID NO 19
<211> LENGTH: 213
<212> TYPE: PRT
<213> ORGANISM: Artificial
<220> FEATURE:
<223> OTHER INFORMATION: Synthetic polypeptide

<400> SEQUENCE: 19

Gln Ile Val Leu Ser Gln Ser Pro Ala Ile Leu Ser Ala Ser Pro Gly
1               5                10               15

Glu Lys Val Thr Met Thr Cys Arg Ala Ser Ser Ser Val Ser Tyr Ile
             20               25               30

His Trp Phe Gln Gln Lys Pro Gly Ser Ser Pro Lys Pro Trp Ile Tyr
        35               40               45

Ala Thr Ser Asn Leu Ala Ser Gly Val Pro Val Arg Phe Ser Gly Ser
    50               55               60

Gly Ser Gly Thr Ser Tyr Ser Leu Thr Ile Ser Arg Val Glu Ala Glu
65               70               75               80

Asp Ala Ala Thr Tyr Tyr Cys Gln Gln Trp Thr Ser Asn Pro Pro Thr
             85               90               95

Phe Gly Gly Gly Thr Lys Leu Glu Ile Lys Arg Thr Val Ala Ala Pro
             100              105              110

Ser Val Phe Ile Phe Pro Pro Ser Asp Glu Gln Leu Lys Ser Gly Thr
        115              120              125

Ala Ser Val Val Cys Leu Leu Asn Asn Phe Tyr Pro Arg Glu Ala Lys
    130              135              140

Val Gln Trp Lys Val Asp Asn Ala Leu Gln Ser Gly Asn Ser Gln Glu
145              150              155              160

Ser Val Thr Glu Gln Asp Ser Lys Asp Ser Thr Tyr Ser Leu Ser Ser
             165              170              175

Thr Leu Thr Leu Ser Lys Ala Asp Tyr Glu Lys His Lys Val Tyr Ala
             180              185              190

Cys Glu Val Thr His Gln Gly Leu Ser Ser Pro Val Thr Lys Ser Phe
        195              200              205

Asn Arg Gly Glu Cys
    210
```

```
<210> SEQ ID NO 20
<211> LENGTH: 219
<212> TYPE: PRT
```

```
<213> ORGANISM: Artificial
<220> FEATURE:
<223> OTHER INFORMATION: Synthetic polypeptide

<400> SEQUENCE: 20

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 21
<211> LENGTH: 120
<212> TYPE: PRT
<213> ORGANISM: Artificial
<220> FEATURE:
<223> OTHER INFORMATION: Synthetic polypeptide

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Leu Ile Ile Pro Met Phe Asp Thr Ala Gly Tyr Ala Gln Lys Phe
    50                  55                  60

Gln Gly Arg Val Ala Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu His Ser Ser Thr Gly Thr Phe Asp Tyr Trp Gly Gln
            100                 105                 110
```

-continued

```
Gly Thr Leu Val Thr Val Ser Ser
        115                 120

<210> SEQ ID NO 22
<211> LENGTH: 98
<212> TYPE: PRT
<213> ORGANISM: Artificial
<220> FEATURE:
<223> OTHER INFORMATION: Synthetic polypeptide

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 23
<211> LENGTH: 15
<212> TYPE: PRT
<213> ORGANISM: Artificial
<220> FEATURE:
<223> OTHER INFORMATION: Synthetic polypeptide

<400> SEQUENCE: 23

Glu Pro Lys Ser Cys Asp Lys Thr His Thr Cys Pro Pro Cys Pro
1               5                   10                  15

<210> SEQ ID NO 24
<211> LENGTH: 110
<212> TYPE: PRT
<213> ORGANISM: Artificial
<220> FEATURE:
<223> OTHER INFORMATION: Synthetic polypeptide

<400> SEQUENCE: 24

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 25
```

```
<211> LENGTH: 107
<212> TYPE: PRT
<213> ORGANISM: Artificial
<220> FEATURE:
<223> OTHER INFORMATION: Synthetic polypeptide

<400> SEQUENCE: 25

Gly Gln Pro Arg Glu Pro Gln Val Tyr Val Leu Pro Pro Ser Arg Asp
1               5                   10                  15

Asn Leu Thr Lys Asn Gln Val Arg Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Lys Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 26
<211> LENGTH: 129
<212> TYPE: PRT
<213> ORGANISM: Artificial
<220> FEATURE:
<223> OTHER INFORMATION: Synthetic polypeptide

<400> SEQUENCE: 26

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Glu Leu Glu Glu Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gly Asp Ala Ser Ile His Asp
65                  70                  75                  80

Leu Ile Ser Asn Ile Asn Val Ile Val Leu Glu Leu Lys Gly Ser Glu
                85                  90                  95

Thr Thr Phe Met Cys Glu Tyr Ala Asp Glu Thr Ala Thr Ile Val Glu
                100                 105                 110

Phe Leu Asn Arg Trp Ile Thr Phe Ser Gln Ser Ile Ile Ser Thr Leu
        115                 120                 125

Thr

<210> SEQ ID NO 27
<211> LENGTH: 20
<212> TYPE: PRT
<213> ORGANISM: Artificial
<220> FEATURE:
<223> OTHER INFORMATION: Synthetic polypeptide

<400> SEQUENCE: 27

Gly Gly Gly Gly Ser Gly Gly Gly Gly Ser Asp Lys Thr His Thr Cys
1               5                   10                  15

Pro Pro Cys Pro
```

-continued

20

<210> SEQ ID NO 28
<211> LENGTH: 107
<212> TYPE: PRT
<213> ORGANISM: Artificial
<220> FEATURE:
<223> OTHER INFORMATION: Synthetic polypeptide

<400> SEQUENCE: 28

Gly Gln Pro Arg Glu Pro Asp Val Thr Val Leu Pro Pro Ser Arg Asp
1               5                   10                  15

Glu Leu Thr Lys Asn Gln Val Ser Leu Thr Cys Leu Val Ser Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Asp Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 29
<211> LENGTH: 107
<212> TYPE: PRT
<213> ORGANISM: Artificial
<220> FEATURE:
<223> OTHER INFORMATION: Synthetic polypeptide

<400> SEQUENCE: 29

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Glu Leu Arg Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 30
<211> LENGTH: 107
<212> TYPE: PRT
<213> ORGANISM: Artificial
<220> FEATURE:
<223> OTHER INFORMATION: Synthetic polypeptide

<400> SEQUENCE: 30

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Thr Gly Phe
            20                  25                  30

```
Tyr Pro Ser Asp Ile Ala Val Glu Trp Glu Ser Asn Gly Gln Pro Glu
        35                  40                  45

Asn Asn Tyr Lys Thr Thr Pro Pro Val Leu Lys Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 31
<211> LENGTH: 121
<212> TYPE: PRT
<213> ORGANISM: Artificial
<220> FEATURE:
<223> OTHER INFORMATION: Synthetic polypeptide

<400> SEQUENCE: 31

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 32
<211> LENGTH: 107
<212> TYPE: PRT
<213> ORGANISM: Artificial
<220> FEATURE:
<223> OTHER INFORMATION: Synthetic polypeptide

<400> SEQUENCE: 32

Gly Gln Pro Arg Glu Pro Gln Val Tyr Thr Leu Pro Pro Ser Arg Asp
1               5                   10                  15

Asn Leu Thr Lys Asn Gln Val Arg Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Lys Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
```

```
                100                 105

<210> SEQ ID NO 33
<211> LENGTH: 107
<212> TYPE: PRT
<213> ORGANISM: Artificial
<220> FEATURE:
<223> OTHER INFORMATION: Synthetic polypeptide

<400> SEQUENCE: 33

Gly Gln Pro Arg Glu Pro Gln Val Tyr Thr Leu Pro Pro Ser Arg Asp
1               5                   10                  15

Glu Leu Thr Lys Asn Gln Val Arg Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Lys Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 34
<211> LENGTH: 107
<212> TYPE: PRT
<213> ORGANISM: Artificial
<220> FEATURE:
<223> OTHER INFORMATION: Synthetic polypeptide

<400> SEQUENCE: 34

Gly Gln Pro Arg Glu Pro Asp Val Thr Thr Leu Pro Pro Ser Arg Asp
1               5                   10                  15

Glu Leu Thr Lys Asn Gln Val Ser Leu Thr Cys Leu Val Ser Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Asp Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 35
<211> LENGTH: 107
<212> TYPE: PRT
<213> ORGANISM: Artificial
<220> FEATURE:
<223> OTHER INFORMATION: Synthetic polypeptide

<400> SEQUENCE: 35

Gly Gln Pro Arg Glu Pro Gln Val Thr Thr Leu Pro Pro Ser Arg Asp
1               5                   10                  15

Glu Leu Thr Lys Asn Gln Val Ser Leu Thr Cys Leu Val Ser Gly Phe
            20                  25                  30
```

-continued

```
Tyr Pro Ser Asp Ile Ala Val Glu Trp Glu Ser Asn Gly Gln Pro Glu
        35              40              45

Asn Asn Tyr Lys Thr Thr Pro Pro Val Leu Asp Ser Asp Gly Ser Phe
    50              55              60

Phe Leu Tyr Ser Asp Leu Thr Val Asp Lys Ser Arg Trp Gln Gln Gly
65              70              75              80

Asn Val Phe Ser Cys Ser Val Met His Glu Ala Leu His Asn His Tyr
            85              90              95

Thr Gln Lys Ser Leu Ser Leu Ser Pro Gly Lys
            100             105

<210> SEQ ID NO 36
<211> LENGTH: 115
<212> TYPE: PRT
<213> ORGANISM: Artificial
<220> FEATURE:
<223> OTHER INFORMATION: Synthetic polypeptide

<400> SEQUENCE: 36

Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Asp Tyr
            20              25              30

Glu Met His Trp Val Arg Gln Ala Pro Gly Gln Gly Leu Glu Trp Met
        35              40              45

Gly Ala Leu Asp Pro Lys Thr Gly Asp Thr Ala Tyr Ser Gln Lys Phe
    50              55              60

Lys Gly Arg Val Thr Leu Thr Ala Asp Lys Ser Thr Ser Thr Ala Tyr
65              70              75              80

Met Glu Leu Ser Ser Leu Thr Ser Glu Asp Thr Ala Val Tyr Tyr Cys
            85              90              95

Thr Arg Phe Tyr Ser Tyr Thr Tyr Trp Gly Gln Gly Thr Leu Val Thr
            100             105             110

Val Ser Ser
        115

<210> SEQ ID NO 37
<211> LENGTH: 132
<212> TYPE: PRT
<213> ORGANISM: Artificial
<220> FEATURE:
<223> OTHER INFORMATION: Synthetic polypeptide

<400> SEQUENCE: 37

Gln Val Gln Leu Gln Glu Ser Gly Gly Gly Leu Val Gln Pro Gly Gly
1               5               10              15

Ser Leu Arg Leu Ser Cys Ala Ala Ser Ala Tyr Thr Ile Ser Arg Asn
            20              25              30

Ser Met Gly Trp Phe Arg Gln Ala Pro Gly Lys Gly Leu Glu Gly Val
        35              40              45

Ala Ala Ile Glu Ser Asp Gly Ser Thr Ser Tyr Ser Asp Ser Val Lys
    50              55              60

Gly Arg Phe Thr Ile Ser Leu Asp Asn Ser Lys Asn Thr Leu Tyr Leu
65              70              75              80

Glu Met Asn Ser Leu Arg Ala Glu Asp Thr Ala Val Tyr Tyr Cys Ala
            85              90              95

Ala Pro Lys Val Gly Leu Gly Pro Arg Thr Ala Leu Gly His Leu Ala
```

```
            100              105             110
Phe Met Thr Leu Pro Ala Leu Asn Tyr Trp Gly Gln Gly Thr Leu Val
        115                 120                 125

Thr Val Ser Ser
    130

<210> SEQ ID NO 38
<211> LENGTH: 15
<212> TYPE: PRT
<213> ORGANISM: Artificial
<220> FEATURE:
<223> OTHER INFORMATION: Synthetic polypeptide

<400> SEQUENCE: 38

Glu Pro Lys Ser Ser Asp Lys Thr His Thr Cys Pro Pro Cys Pro
1               5                   10                  15

<210> SEQ ID NO 39
<211> LENGTH: 237
<212> TYPE: PRT
<213> ORGANISM: Artificial
<220> FEATURE:
<223> OTHER INFORMATION: Synthetic polypeptide

<400> SEQUENCE: 39

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Val Ser Phe Pro Ile
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gln Val Gln Leu Gln Glu
            115                 120                 125

Ser Gly Pro Gly Leu Val Lys Pro Ser Glu Thr Leu Ser Leu Thr Cys
    130                 135                 140

Thr Val Ser Gly Gly Ser Ile Glu His Tyr Tyr Trp Ser Trp Ile Arg
145                 150                 155                 160

Gln Pro Pro Gly Lys Gly Leu Glu Trp Ile Gly Tyr Ile Tyr Tyr Ser
                165                 170                 175

Gly Ser Thr Asn Tyr Asn Pro Ser Leu Lys Ser Arg Val Thr Ile Ser
            180                 185                 190

Val Asp Thr Ser Lys Asn Gln Phe Ser Leu Lys Leu Ser Ser Val Thr
            195                 200                 205

Ala Ala Asp Thr Ala Val Tyr Tyr Cys Ala Arg Gly Lys Thr Gly Ser
    210                 215                 220

Ala Ala Trp Gly Gln Gly Thr Leu Val Thr Val Ser Ser
225                 230                 235

<210> SEQ ID NO 40
<211> LENGTH: 10
```

```
<212> TYPE: PRT
<213> ORGANISM: Artificial
<220> FEATURE:
<223> OTHER INFORMATION: Synthetic polypeptide

<400> SEQUENCE: 40

Asp Lys Thr His Thr Cys Pro Pro Cys Pro
1               5               10

<210> SEQ ID NO 41
<211> LENGTH: 120
<212> TYPE: PRT
<213> ORGANISM: Artificial
<220> FEATURE:
<223> OTHER INFORMATION: Synthetic polypeptide

<400> SEQUENCE: 41

Glu Val Gln Leu Val Glu Ser Gly Gly Gly Leu Val Gln Pro Gly Gly
1               5               10              15

Ser Leu Arg Leu Ser Cys Ala Ala Ser Gly Phe Asn Ile Lys Asp Thr
            20              25              30

Tyr Ile His Trp Val Arg Gln Ala Pro Gly Lys Gly Leu Glu Trp Val
        35              40              45

Ala Arg Ile Tyr Pro Thr Asn Gly Tyr Thr Arg Tyr Ala Asp Ser Val
    50              55              60

Lys Gly Arg Phe Thr Ile Ser Ala Asp Thr Ser Lys Asn Thr Ala Tyr
65              70              75              80

Leu Gln Met Asn Ser Leu Arg Ala Glu Asp Thr Ala Val Tyr Tyr Cys
            85              90              95

Ser Arg Trp Gly Gly Asp Gly Phe Tyr Ala Met Asp Tyr Trp Gly Gln
            100             105             110

Gly Thr Leu Val Thr Val Ser Ser
        115             120

<210> SEQ ID NO 42
<211> LENGTH: 107
<212> TYPE: PRT
<213> ORGANISM: Artificial
<220> FEATURE:
<223> OTHER INFORMATION: Synthetic polypeptide

<400> SEQUENCE: 42

Asp Ile Gln Met Thr Gln Ser Pro Ser Ser Val Ser Ala Ser Val Gly
1               5               10              15

Asp Arg Val Thr Ile Thr Cys Arg Ala Ser Gln Gly Ile Ser Ser Trp
            20              25              30

Leu Ala Trp Tyr Gln Gln Lys Pro Gly Lys Ala Pro Lys Leu Leu Ile
        35              40              45

Ser Ala Ala Ser Ser Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ala Asn His Leu Pro Phe
            85              90              95

Thr Phe Gly Gly Gly Thr Lys Val Glu Ile Lys
            100             105

<210> SEQ ID NO 43
<211> LENGTH: 107
<212> TYPE: PRT
```

<213> ORGANISM: Artificial
<220> FEATURE:
<223> OTHER INFORMATION: Synthetic polypeptide

<400> SEQUENCE: 43

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 44
<211> LENGTH: 107
<212> TYPE: PRT
<213> ORGANISM: Artificial
<220> FEATURE:
<223> OTHER INFORMATION: Synthetic polypeptide

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 45
<211> LENGTH: 106
<212> TYPE: PRT
<213> ORGANISM: Artificial
<220> FEATURE:
<223> OTHER INFORMATION: Synthetic polypeptide

<400> SEQUENCE: 45

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

-continued

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 46
<211> LENGTH: 112
<212> TYPE: PRT
<213> ORGANISM: Artificial
<220> FEATURE:
<223> OTHER INFORMATION: Synthetic polypeptide

<400> SEQUENCE: 46

Asp Val Val Met Thr Gln Ser Pro Leu Ser Leu Pro Val Thr Pro Gly
1                   5                   10                  15

Glu Pro Ala Ser Ile Ser Cys Arg Ser Ser Gln Ser Leu Val His Ser
                20                  25                  30

Asn Arg Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 47
<211> LENGTH: 330
<212> TYPE: PRT
<213> ORGANISM: Artificial
<220> FEATURE:
<223> OTHER INFORMATION: Synthetic polypeptide

<400> SEQUENCE: 47

Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp

-continued

```
145              150              155              160

Tyr Val Asp Gly Val Glu Val His Asn Ala Lys Thr Lys Pro Arg Glu
             165              170              175

Glu Gln Tyr Asn Ser Thr Tyr Arg Val Val Ser Val Leu Thr Val Leu
             180              185              190

His Gln Asp Trp Leu Asn Gly Lys Glu Tyr Lys Cys Lys Val Ser Asn
             195              200              205

Lys Ala Leu Pro Ala Pro Ile Glu Lys Thr Ile Ser Lys Ala Lys Gly
     210              215              220

Gln Pro Arg Glu Pro Gln Val Tyr Thr Leu Pro Pro Ser Arg Asp Glu
225              230              235              240

Leu Thr Lys Asn Gln Val Ser Leu Thr Cys Leu Val Lys Gly Phe Tyr
             245              250              255

Pro Ser Asp Ile Ala Val Glu Trp Glu Ser Asn Gly Gln Pro Glu Asn
             260              265              270

Asn Tyr Lys Thr Thr Pro Pro Val Leu Asp Ser Asp Gly Ser Phe Phe
             275              280              285

Leu Tyr Ser Lys Leu Thr Val Asp Lys Ser Arg Trp Gln Gln Gly Asn
     290              295              300

Val Phe Ser Cys Ser Val Met His Glu Ala Leu His Asn His Tyr Thr
305              310              315              320

Gln Lys Ser Leu Ser Leu Ser Pro Gly Lys
             325              330
```

```
<210> SEQ ID NO 48
<211> LENGTH: 227
<212> TYPE: PRT
<213> ORGANISM: Artificial
<220> FEATURE:
<223> OTHER INFORMATION: Synthetic polypeptide

<400> SEQUENCE: 48

Asp Lys Thr His Thr Cys Pro Pro Cys Pro Ala Pro Glu Leu Leu Gly
1               5               10              15

Gly Pro Ser Val Phe Leu Phe Pro Pro Lys Pro Lys Asp Thr Leu Met
             20              25              30

Ile Ser Arg Thr Pro Glu Val Thr Cys Val Val Val Asp Val Ser His
             35              40              45

Glu Asp Pro Glu Val Lys Phe Asn Trp Tyr Val Asp Gly Val Glu Val
             50              55              60

His Asn Ala Lys Thr Lys Pro Arg Glu Glu Gln Tyr Asn Ser Thr Tyr
65              70              75              80

Arg Val Val Ser Val Leu Thr Val Leu His Gln Asp Trp Leu Asn Gly
             85              90              95

Lys Glu Tyr Lys Cys Lys Val Ser Asn Lys Ala Leu Pro Ala Pro Ile
             100             105             110

Glu Lys Thr Ile Ser Lys Ala Lys Gly Gln Pro Arg Glu Pro Gln Val
             115             120             125

Tyr Thr Leu Pro Pro Ser Arg Asp Glu Leu Thr Lys Asn Gln Val Ser
             130             135             140

Leu Thr Cys Leu Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
             165             170             175

Val Leu Asp Ser Asp Gly Ser Phe Phe Leu Tyr Ser Lys Leu Thr Val
```

-continued

```
                180                 185                 190
Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 49
<211> LENGTH: 107
<212> TYPE: PRT
<213> ORGANISM: Artificial
<220> FEATURE:
<223> OTHER INFORMATION: Synthetic polypeptide

<400> SEQUENCE: 49

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
                100                 105
```